US011179459B1

United States Patent
Jang et al.

(10) Patent No.: US 11,179,459 B1
(45) Date of Patent: Nov. 23, 2021

(54) VACCINE COMPOSITION FOR PREVENTING HUMAN INFECTION OF SARS CORONAVIRUS AND ALLEVIATING INFECTION SYMPTOMS

(71) Applicant: LIBENTECH CO., LTD., Daejeon (KR)

(72) Inventors: Hyun Jang, Ansan-si (KR); Bo-Kyoung Jung, Busan (KR); Yong-Hee An, Sejong (KR)

(73) Assignee: LIBENTECH CO., LTD., Daejeon (KR)

( * ) Notice: Subject to any disclaimer, the term of this patent is extended or adjusted under 35 U.S.C. 154(b) by 0 days.

(21) Appl. No.: 17/354,470

(22) Filed: Jun. 22, 2021

Related U.S. Application Data

(63) Continuation of application No. PCT/KR2021/003046, filed on Mar. 11, 2021.

(30) Foreign Application Priority Data

Jan. 28, 2021 (KR) .................. 10-2021-0012238

(51) Int. Cl.
| | |
|---|---|
| *A61K 39/215* | (2006.01) |
| *A61P 31/14* | (2006.01) |
| *A61K 39/39* | (2006.01) |
| *C12N 7/00* | (2006.01) |
| *C12N 15/86* | (2006.01) |
| *G01N 33/68* | (2006.01) |
| *A61K 39/00* | (2006.01) |

(52) U.S. Cl.
CPC ............ *A61K 39/215* (2013.01); *A61K 39/39* (2013.01); *A61P 31/14* (2018.01); *C12N 7/00* (2013.01); *C12N 15/86* (2013.01); *G01N 33/6854* (2013.01); *A61K 2039/5252* (2013.01); *A61K 2039/5254* (2013.01); *A61K 2039/5256* (2013.01); *C12N 2760/18121* (2013.01); *C12N 2760/18134* (2013.01); *C12N 2760/18143* (2013.01); *C12N 2760/18152* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

2017/0224807 A1* 8/2017 Bublot .................... A61P 31/12

OTHER PUBLICATIONS

Alignment of instant SEQ ID No. 3 with Oct. 2020 UniProt database accession No. A0A6M8WHE5_SARS2.*
Zhao et al. (Journal of General Virology. 2003; 84: 781-788).*
Shirvani et al. (Pathogens. Jul. 2020; 9: 619: 1-8).*
Pan et al. (PLOS One. Oct. 2016; DOI:10.1371/journal.pone. 0164723: 1-13).*
Wang et al. (Frontiers in Microbiology. Feb. 2020; 11, Article 298).*
Alignment of nucleic acid residue Nos. 200-4000 of SEQ ID No. 1 with Aug. 2017 Geneseq database accession No. BEF10759 by Bublot et al. in USPgPub 2017/0224807.*

* cited by examiner

*Primary Examiner* — Shanon A. Foley
(74) *Attorney, Agent, or Firm* — Sughrue Mion, PLLC

(57) ABSTRACT

The present disclosure relates to a vaccine composition for preventing human infection SARS-CoV-2 (COVID-19) and alleviating infection symptoms, and the vaccine composition including a recombinant Newcastle disease virus on the surface of which the SARS-CoV-2 RBD protein of the present disclosure is expressed or antigen purified therefrom induces an immune response that can fight COVID-19 infection so that it can be useful as a vaccine for preventing and treating SARS-CoV-2 infection.

19 Claims, 8 Drawing Sheets

Specification includes a Sequence Listing.

[FIG 1A]
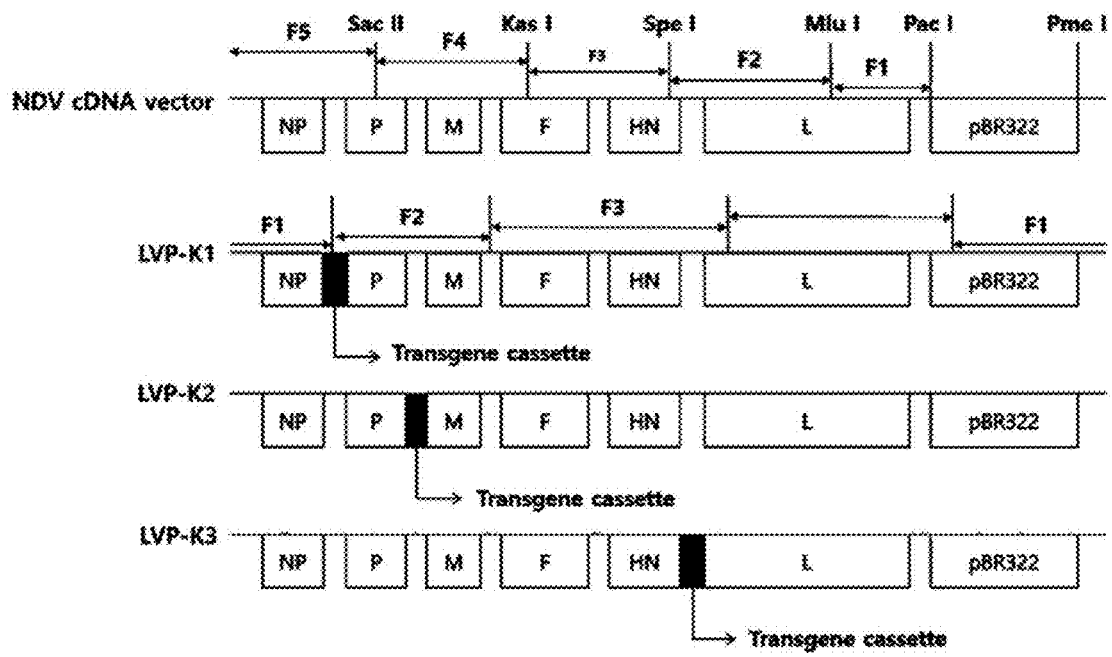
[FIG 1B]
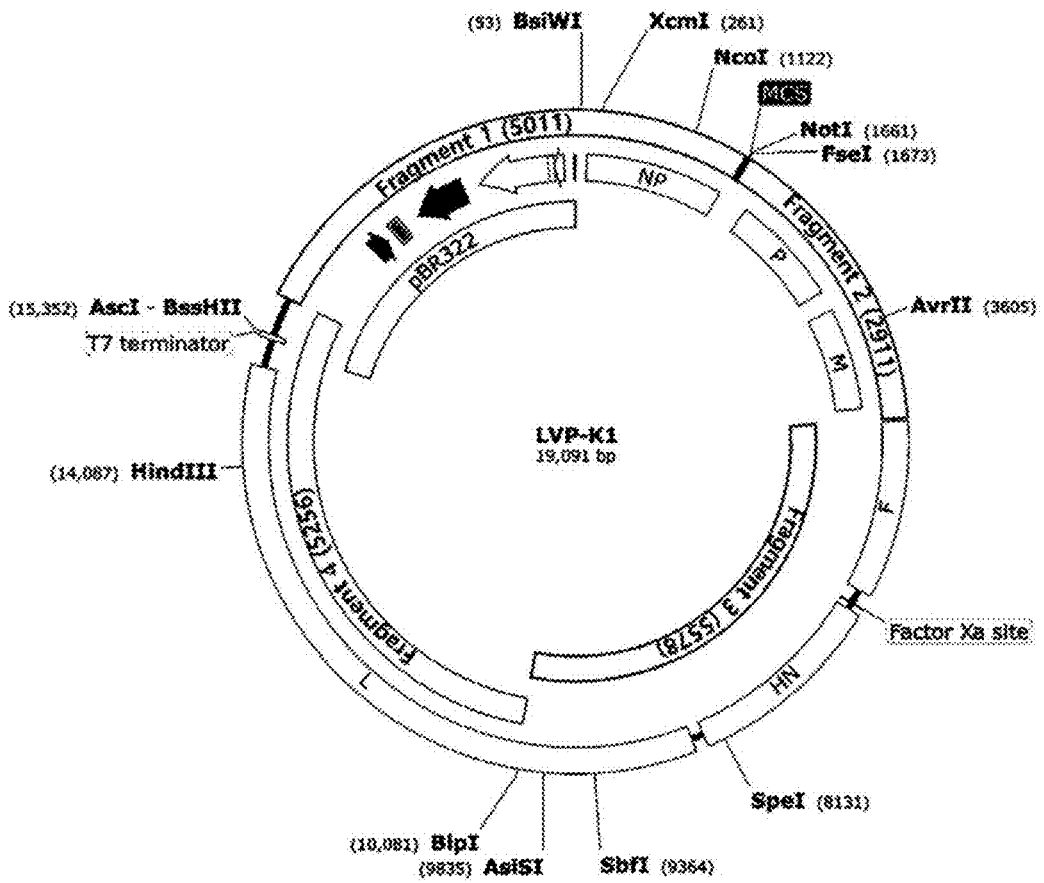

[FIG 1C]
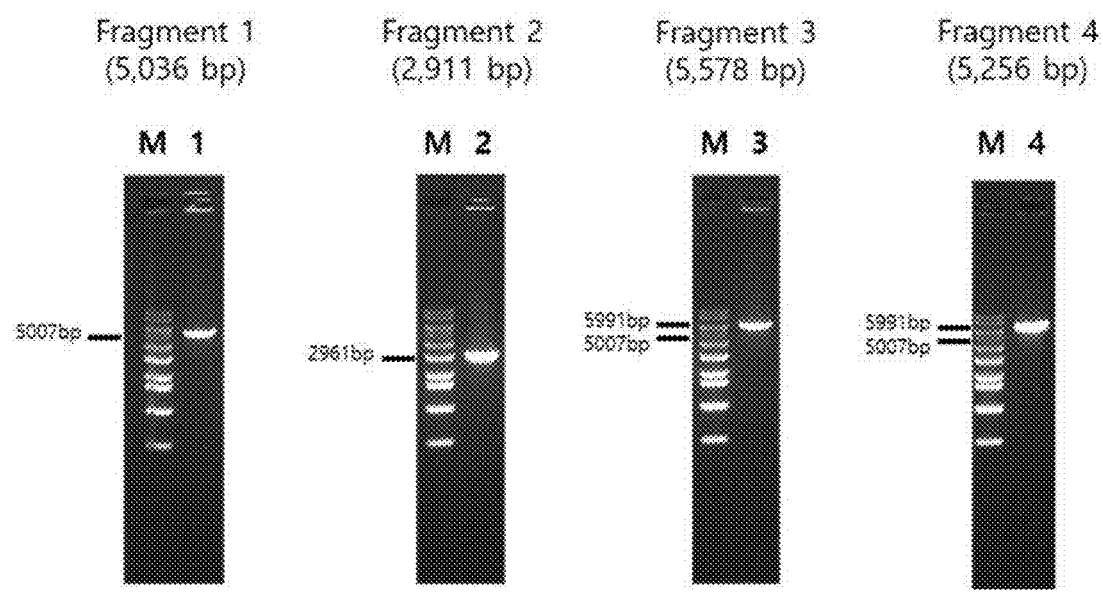
[FIG 2]
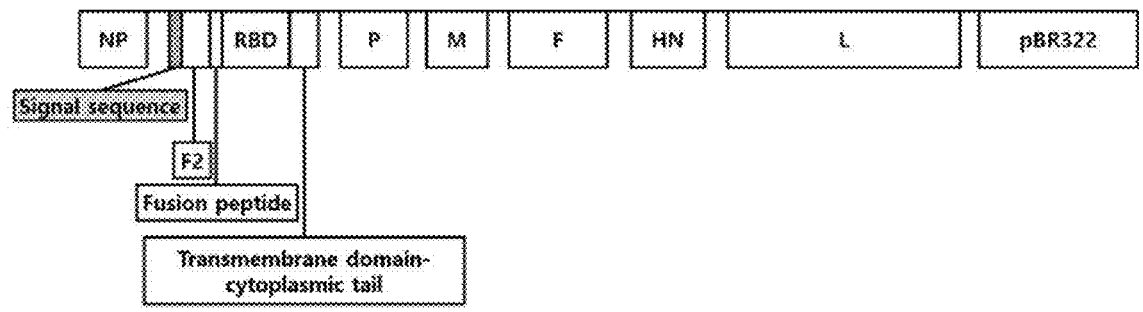

Virus inactivation

[FIG 5A]

RBD protein

LVP-K1-RBD19

Total IgG

[FIG 6B]

LVP-K1-RBD19 ($10^7$ TCID$_{50}$/dose)

[FIG 7A]

Body weight

[FIG 7B]

Food intake

[FIG 7C]

Water intake

[FIG 7D]

VACCINE COMPOSITION FOR PREVENTING HUMAN INFECTION OF SARS CORONAVIRUS AND ALLEVIATING INFECTION SYMPTOMS

CROSS-REFERENCE TO RELATED APPLICATIONS

This application is a continuation application of, and claims priority from International Application No. PCT/KR2021/003046 filed Mar. 11, 2021, claiming priority from Korean Patent Application No. 10-2021-0012238, filed Jan. 28, 2021, the entire disclosures of which are incorporated herein by reference.

TECHNICAL FIELD

The present disclosure relates to a vaccine composition for preventing human infection of SARS coronavirus (severe acute respiratory syndrome coronavirus 2; SARS-CoV-2; COVID-19) and alleviating infection symptoms.

BACKGROUND

Acute respiratory syndrome is an infectious disease caused by Severe Acute Respiratory Syndrome Coronavirus 2 (SARS-CoV-2) infection, and the first case of infection was reported in Wuhan, China in December 2019. Pneumonia symptoms occurred mainly among those who visited the seafood market located in Hunnan, Wuhan. The virus was isolated from a patient by a scientist in Wuhan, and genetic analysis indicated that it was a new coronavirus rather than the existing SARS-CoV and MERS-CoV. On Feb. 1, 2020, 11,821 cases were reported in China, and there were already 132 confirmed cases in 23 countries including China. After that, the virus, which was named SARS-CoV-2, spread rapidly around the world. Currently, more than 80 million people have been infected by the virus worldwide and more than 1.6 million people have died as a result. In South Korea, more than 44,000 people were infected, 600 people died, and about 1,000 people are infected every day. The main symptoms of SARS-CoV-2 infection include fever, dry cough, fatigue, and, depending on the person, body aches, headache, diarrhea, sore throat, and loss of taste or smell. However, there are many infected people who do not have specific symptoms after being infected with the virus. The virus propagates very quickly, and the current fatality rate is 1.36% in South Korea and 2.23% worldwide, which is a marked decrease compared to the initial fatality rate. Nevertheless, the rate of transmission of the virus is proceeding very rapidly, resulting in the largest number of infections and deaths due to a pandemic disease since the Spanish flu of 1918. SARS-CoV-2 is a beta-coronavirus that infects humans, belongs to the coronavirus family, and has a single-stranded RNA genome. The total genome size is 30,473 bp, which is not small. The total gene has 10 genes from ORF1a to ORF10. Viral genes are divided into non-structural genes and structural genes, and the S gene is known as a spike glycoprotein that binds to the ACE2 receptor in the human respiratory system. SARS-CoV-2 has first detected as a type A virus, but it was later found to be prevalent in North America and Europe. In the case of type B, it is mainly detected in East Asia, and in the case of type C, it is spread in Europe and several countries in Asia including South Korea. There is no difference in serotypes based on the virus genotype, but as the infection continues, viruses of different genotypes are being detected in each country. In the case of the recently isolated (UK VOC202012/01, B,1,1,7) mutant strain from the UK, two amino acid sequence mutations were confirmed in the ACE-2 receptor binding domain gene sequence, and the mutant strain with three amino acid sequence mutations also occurred in Brazil and South Africa. Amino acid mutations in the receptor binding domain sequence necessitate retesting the efficacy of previously developed vaccines, and further consideration is required to determine if vaccine development is necessary for these mutations. As a result of analyzing the genome of SARS-CoV-2, SARS-CoV-2 is beta-coronavirus belonging to the same family as SARS-CoV (Severe acute respiratory syndrome coronavirus) and has an RNA genome of 30 kb, so it turned out that SARS-CoV-2 has the largest RNA genome among RNA viruses. The genome of SARS-CoV-2 consists of 10 genes, and 2/3 of the entire genome is ORF lab, which is a non-structural protein (NSP). The remaining 3' terminus gene has four structural protein genes, which are spike (S), envelope (E), matrix (M), and nucleocapsid (N). In addition, SARS-CoV-2 has five accessory protein genes (ORF3, 6, 7a, 7b, 8, 10). Among them, the gene of ORF10 has not yet been clearly identified.

In SARS-CoV-2 infection, the spike protein on the surface of the virus binds to the angiotensin converting enzyme2 (ACE2) receptor on the surface of the host cell. After that, the TMPRSS2 protein is further bound, the middle part of the spike protein is cut off, and the virus genome is introduced into the cell through the fusion of the cell membrane and the virus membrane, after which the virus multiplies. The ACE2 enzyme is expressed in major organs, including the heart, lungs, kidneys, vascular endothelium, and digestive system.

There is an urgent need to develop a vaccine against SARS-CoV-2 (COVID-19), which involves a development process that has not previously been completed in under a year. More than 25 pharmaceutical companies are developing vaccines in various formulations, and they are vaccines using the mRNA of the already-supplied vaccine. Due to the absolute time limit, it is unclear how much efficacy and safety the vaccine will be guaranteed in a situation where extensive clinical results for the vaccine supplied through expedited approval come out at the same time as the vaccination. Therefore, even if it takes time, a classical form of vaccine must also be developed, and it is also necessary to develop a technology capable of developing a vaccine quickly in order to prepare for a continuous new infectious disease. When it comes to vaccines targeting people around the world, vaccine production and economics are very important. The development of technology is of paramount importance so that vaccines can be utilized with equity and accessible to all of humanity. In particular, this SARS-CoV-2 (COVID-19) pandemic is a significant time in which humanity has been put to the test of whether it is possible to control the disease through a vaccine. Viral vector vaccines are sometimes used as vaccines in a live form by expressing a protein that transfers an antigenic gene to a virus that is not pathogenic to the human body to induce an immune response or by expressing an antigenic protein on the surface of a virus, and in some cases, the antigen protein is expressed on the surface of the virus and inactivated to be used as a vaccine. Although it takes time to genetically engineer a virus and create a recombinant virus, it is easy to express different antigens in a successful viral vector, which will be a very important technique for preventing new infectious diseases that may occur in the future. This study intends to develop a vaccine by making a recombinant virus by inserting it into NDV cDNA using certain domain genes of the surface-expressed protein of NDV virus that do not infect mammals and the receptor binding domain (RBD) protein genes of SARS-CoV-2. In addition, this study seeks to develop a virus vector platform that can express various antigens in specific regions of these cDNAs.

SUMMARY

The present disclosure has been made in an effort to provide an LVP-K1 vector for insertion of a foreign gene including Newcastle disease virus cDNA and transgene cassette.

Further, the present disclosure has been made in an effort to provide a recombinant Newcastle disease virus including LVP-K1 vector for insertion of a foreign gene and a receptor binding domain (RBD) of SARS-CoV-2 virus spike protein.

Further, the present disclosure has been made in an effort to provide a vaccine composition for preventing or treating SARS coronavirus (SARS-CoV-2) including the recombinant Newcastle disease virus or antigen purified from the virus.

Further, the present disclosure has been made in an effort to provide a method of preventing or treating a SARS coronavirus (SARS-CoV-2) infection.

Further, the present disclosure has been made in an effort to provide a method of producing a recombinant Newcastle disease virus.

Further, the present disclosure has been made in an effort to provide a method of evaluating an immune response in an animal, An exemplary embodiment of the present disclosure provides LVP-K1 vector for insertion of a foreign gene including Newcastle disease virus cDNA including genes encoding NP, P, M, F, HN and L proteins and transgene cassette, in which the transgene cassette includes an IGS sequence (Gene end (GE), Intergenic sequence (IG), and Gene start (GS)) and MCS (multicloning site).

Another exemplary embodiment of the present disclosure provides a recombinant Newcastle disease virus including LVP-K1 vector for insertion of a foreign gene and a gene encoding a receptor binding domain (RBD) of SARS-CoV-2 spike protein.

Yet another exemplary embodiment of the present disclosure provides a vaccine composition for preventing or treating SARS coronavirus (SARS-CoV-2), the composition including the recombinant Newcastle disease virus or antigen purified from the virus.

Still another exemplary embodiment of the present disclosure provides a method of preventing or treating a SARS coronavirus (SARS-CoV-2) infection, the method including administering the vaccine composition to an individual.

Yet another exemplary embodiment of the present disclosure provides a method of producing a recombinant Newcastle disease virus, the method including steps: inoculating a host cell line with the recombinant Newcastle disease virus; culturing the host cell line; and obtaining a recombinant Newcastle disease virus from the culture of the host cell line.

Still another exemplary embodiment of the present disclosure provides a method of evaluating an immune response in an animal, the method including administering the recombinant Newcastle disease virus to the animal.

According to the exemplary embodiments of the present disclosure, the vaccine composition including a recombinant Newcastle disease virus on the surface of which the SARS-CoV-2 RBD protein is expressed, or antigen purified therefrom induces an immune response that may fight COVID-19 infection so that it may be useful as a vaccine for preventing and treating SARS-CoV-2 infection.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1A is a schematic diagram showing the gene of the LVP-K1 vector of the present disclosure, FIG. 1B shows a vector map, and FIG. 1C shows a PCR product of the present disclosure;

FIG. 2 is a schematic diagram of the gene of LVP-K1-RBD19 of the present disclosure;

FIG. 3A is a view showing the results of the RBD protein surface expression analysis of LVP-K1-RBD19 of the present disclosure;

FIG. 3B is a view showing the results of the RBD protein surface expression analysis of LVP-K1-RBD19 of the present disclosure;

FIG. 4 is a view showing the results of time-dependent virus titer analysis after inactivation of LVP-K1-RBD19 of the present disclosure;

FIG. 5A is a view showing the results of a sandwich ELISA for measuring the amount of RBD protein expressed on the surface of LVP-K1-RBD19 of the present disclosure;

FIG. 5B is a view showing the results of a sandwich ELISA for measuring the amount of RBD protein expressed on the surface of LVP-K1-RBD19 of the present disclosure;

FIG. 6A is a view showing the results of the RBD protein-specific antibody production analysis of LVP-K1-RBD19 of the present disclosure;

FIG. 6B is a view showing the results of the RBD protein-specific antibody production analysis of LVP-K1-RBD19 of the present disclosure;

Figures 7B, 7C:
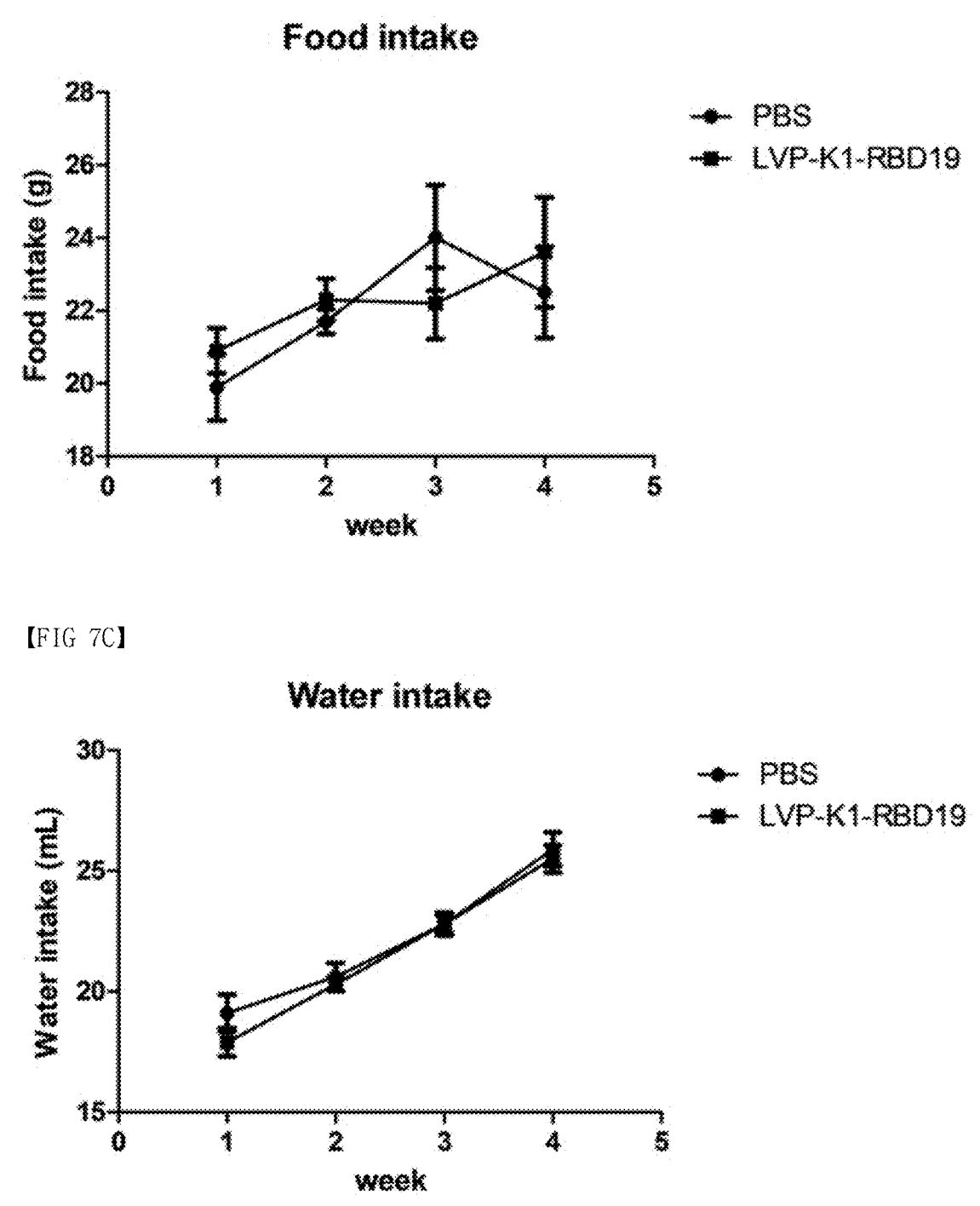

FIG. 7A is a view showing results of the stability evaluation of LVP-K1-RBD19 of the present disclosure;

FIG. 7B is a view showing results of the stability evaluation of LVP-K1-RBD19 of the present disclosure;

FIG. 7C is a view showing results of the stability evaluation of LVP-K1-RBD19 of the present disclosure; and FIG. 7D is a view showing results of the stability evaluation of LVP-K1-RBD19 of the present disclosure.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure is described in more detail.

In order to achieve the above object, the present disclosure provides an LVP-K1 vector for insertion of a foreign gene including a Newcastle disease virus cDNA including genes encoding NP, P, M, F, HN and L proteins and a transgene cassette.

Further, the transgene cassette may include an IGS sequence (Gene end (GE), Intergenic sequence (IG), and Gene start (GS)) and MCS (multicloning site).

The term "Newcastle disease virus (NDV)" used in the present disclosure belongs to a paramyxovirus having a (−) sense RNA genome of about 15 kb and is known as a virus that is safe for mammals without human infectivity. NDV genomic RNA has an extragenic leader sequence of about 30 bases and a tail sequence of about 50 bases. Two sequences at both ends are known to regulate the transcription and replication of viral genes and the encapsulation of newly synthesized RNA genomes into viral particles. The NDV gene consists of six genes including NP, P, M, F, HN and L between both terminal leader and tail genes, and the six genes encode a nucleoprotein (NP), phosphoprotein (P), matrix protein (M), fusion protein (F), hemagglutinin-neuraminidase protein (HN), and large protein (L), respectively.

In the Newcastle disease virus, IGS [Gene end (GE), Intergenic sequence (IG), Gene start (GS)] sequences exist between each gene. In the initial stage of host cell infection, each gene undergoes transcription and moves to the endoplasmic reticulum (ER) of the host cell to synthesize proteins. Afterward, when the amount of M protein synthesis exceeds a certain level, a (+) sense RNA genome is synthesized, and a (−) sense RNA genome is synthesized using this as a template. The complete virus particles are released out of the cell.

It is known that the Newcastle disease virus has a foreign gene introduction capability of up to 6 kb, and foreign gene introduction has been mainly made between P and M genes and between HN and L genes. However, it is known that foreign genes may be introduced between all of the six genes, but each position affects mRNA expression, protein expression, and, in severe cases, virus proliferation. However, a quantitative comparison test according to each location has not been performed. There is a GE-IG-GS gene between each gene. In particular, in the case of an IG gene, it has 1 or 2 nucleotides between NP-P, P-M, and M-F, 35 nucleotides between F-HN and 47 nucleotides between HN-L. After virus infection, the (−) sense RNA genome synthesizes the mRNA of each protein at the initial stage of infection by the NP, L, and P proteins possessed by NDV, and the synthesized mRNA moves to the endoplasmic reticulum of the host cell to synthesize the protein of each gene. Thereafter, the (+) sense RNA genome is synthesized by the interaction of NP, L, P and M proteins, and many copies of the (−) sense RNA genome are synthesized using this as a template and released out of the host cell. It is known that the amount of mRNA synthesis for autologous protein production at the time of initial infection is greatest from the N-terminus, that is, NP mRNA is synthesized the most, and mRNA synthesis decreases as the distance from the N-terminus increases.

To construct the cDNA of Newcastle disease virus, the NDV (−) sense RNA genome is made into multiple fragments of double-stranded DNA through the reverse transcription polymerase chain reaction (RT-PCR) method, and then each fragment is re-ligated to create a cDNA clone of the entire NDV. cDNA construction using this method has a high possibility of point mutation due to the nature of reverse transcriptase. Therefore, after constructing all cDNAs, the 15 kb gene sequence is confirmed through sequencing, and if one or more point mutations occur, the process of constructing cDNA from the NDV genome must be repeated again. cDNA fragment is inserted into the pBR322 vector to construct a recombinant NDV.

In addition, a transgene cassette is created and inserted so that a foreign gene may be easily introduced into a position where the foreign gene can be inserted so as to express or operate the antigen protein through the recombinant Newcastle disease virus. The transgene cassette is composed of a GE-IG-GS sequence and a multi cloning site (MCS) in front of the N-terminus of the foreign gene insertion site. In accordance with the rule of six along with various restriction enzymes, it may be constructed to be inserted between NP and P genes, between P and M genes, and between HN and L genes. Preferably, it may be inserted between the NP and P genes, between the P and M genes, and more preferably, it may be inserted between the NP and P genes.

According to an embodiment of the present disclosure, the LVP-K1 vector for foreign gene insertion is obtained by the following process: the transgene cassette is added between each gene in a perfectly made recombinant NDV, they are divided into four fragments of DNA, each NDV fragment gene is ligated to pBR322 plasmid DNA, they are transformed into TOP10 E. coli to construct and store four recombinant strains, when introducing a new gene, the gene is separated from each recombinant E. coli strain, then a fragment is obtained using such gene by PCR, and a recombinant NDV virus is constructed through the overlap cloning method, but is not limited thereto.

In addition, the vector prepared by the above method has a feature that it prevents point mutation that occurs during the process of constructing recombinant Newcastle disease virus each time and that a foreign gene may be easily inserted into the NDV cDNA through a multi cloning site (MCS).

In addition, the LVP-K1 vector for foreign gene insertion may be composed of the nucleotide sequence represented by SEQ ID NO: 1 and includes a functionally equivalent substance thereto. The term "functionally equivalent substance" refers to a sequence having at least 70% or more, preferably 80% or more, more preferably 90% or more sequence homology with the gene sequence represented by SEQ ID NO: 1 as a result of nucleotide substitution deletion, which refers to a gene or gene combination that exhibits substantially the same physiological activity as the gene having the gene sequence represented by SEQ ID NO: 2.

Next, the present disclosure provides a recombinant Newcastle disease virus including the LVP-K1 vector for insertion of the foreign gene and the gene encoding the receptor binding domain (RBD) of the SARS-CoV-2 spike protein.

In addition, the gene encoding the SARS-CoV-2 spike protein is a gene of the SARS-CoV-2 having ACE2 binding ability, which is a gene established based on the 2020 Korean SARS-CoV-2 gene information (GeneBank accession No. MT039890.1 SNU01, Severe Acute respiratory syndrome coronavirus 2 isolate BetaCoV/Korea/SNU01/2020).

In addition, the SARS coronavirus (SARS-CoV-2) spike protein refers to a protein expressed in the SARS coronavirus (SARS-CoV-2), which may preferably be the S1 domain of the spike protein, which is a site binding to the ACE2 receptor, more preferably RBD domain, which is a site that directly binds to the ACE2 receptor among the S1 domains, which may be a gene sequence encoding an amino acid sequence of spike protein 319 to 541, even more preferably, the gene sequence encoding the amino acid sequence of spike protein 328 to 524, and most preferably the amino acid sequence represented by SEQ ID NO: 3.

The method for preparing the gene encoding the receptor binding domain (RBD) of the SARS-CoV-2 spike protein is artificially synthesized using a gene synthesizer, or constructed using PCR primers, which is capable of complementary binding from the SARS-CoV-2 genes by reverse transcription polymerase chain reaction (RT-PCR) method. Due to codon-optimization depending on the expression system, it may be different from the gene encoding the SARS-CoV-2 spike protein, so the gene encoding the recombinant receptor binding domain (RBD) may exist in the form of various nucleotide sequences including amino acid residues 319 to 541 of the SARS-CoV-2 spike protein.

The host cell into which the receptor binding domain (RBD) of the SARS-CoV-2 spike protein is introduced may be a prokaryotic or eukaryotic cell. If the introduced SARS-CoV-2 spike protein expression rate is high, the cell can be used without limitation. For example, the cell includes E. coli, mammalian cell lines, insect cell lines, fungi, yeast, eukaryotic and prokaryotic hosts such as recombinant viruses, and the like.

In addition, the receptor binding domain (RBD) of the SARS-CoV-2 spike protein may be expressed as a simple subunit protein or the expressed protein may exist in a form that is exposed to the outside by binding to the surface of a specific cell line or virus line. Preferably, it is expressed on the surface of a cell line or virus line, and may be a fusion protein bound to a protein of an existing cell membrane or virus membrane, or may be a protein independently bound to a cell membrane or a virus membrane, preferably a protein independently expressed to the surface of a cell membrane or a virus membrane, and most preferably, an RBD protein containing a transmembrane domain in the viral envelope, which is sufficiently exposed to the outside of the virus and can be in a form recognized by the immune system.

A virus for the expression of the receptor binding domain (RBD) of the SARS-CoV-2 spike protein can be any virus which expresses or deliver antigens through the introduction of foreign genes and is capable of high stability, high antigen expression ability and high viral titer production without limitation such as Lentivirus, Retrovirus, Vaccinia virus, Adenovirus, Adeno associated virus, Cytomegalovirus, Sendai virus, Poxvirus, Newcastle disease virus, and Alphavirus. Preferably, the virus may be Poxvirus, Flavivirus, Alphavirus, or Newcastle disease virus as an enveloped virus. More preferably, the virus may be Newcastle disease virus that is a safe virus that does not infect humans and is capable of producing a high viral titer. The enveloped virus has an envelope so that the virus itself can act as an adjuvant, which may be helpful for antibody-inducing ability of antigen. The Newcastle disease virus (NDV) is a legal infectious disease that infects chickens and causes neurological and respiratory symptoms so that it is a very lethal virus for chickens. It is divided into velogenic, mesogenic, and lentogenic viruses according to the pathogenicity, and they can be used in the manufacture of inactivated viral vector vaccines. Preferably, mesogenic, and lentogenic viruses can be used.

In addition, the recombinant Newcastle disease virus may further include an NDV surface expression cassette.

In addition, the NDV surface expression cassette may be composed of genes encoding the F2 subunit, fusion peptide, transmembrane domain, and cytoplasmic tail of Newcastle disease virus fusion protein. Specifically, it may be composed of the C-terminal 56 amino acid sequence including the F2 subunit including the signal sequence of the fusion protein, the F1 fusion peptide, and the transmembrane domain-cytoplasmic tail. In addition, the F2 subunit may further include heptad repeat 4 (HR4).

The term "Newcastle disease virus fusion protein" used in the present disclosure is composed of a total of 553 amino acids, which is synthesized as an F0 precursor protein, in which the precursor protein is cleaved into F1 and F2 proteins for virus and host cell fusion activity. The transmembrane domain (TM) of the F protein is known to be located at the carboxyl group terminus of F1.

The term "signal sequence (SS)" used in the present disclosure refers to an amino acid sequence that plays another important role in expressing a foreign protein included in the F2 portion of the Newcastle disease virus fusion protein on the virus surface and means a protein located at N terminal of the fusion protein.

In the present disclosure, the signal sequence may be up to the 117th amino acid sequence in which the fusion protein cleavage site exists, preferably, an amino acid sequence of 40th or more amino acids from the N-terminus, and more preferably may include up to the 31st amino acid sequence from the N-terminus.

In addition, the signal sequence may be composed of the nucleotide sequence represented by SEQ ID NO: 5 and includes all functionally equivalent substances thereto. The term "functionally equivalent substance" refers to a substance having at least 70% or more, preferably 80% or more, more preferably 90% or more sequence homology with the amino acid sequence represented by SEQ ID NO: 5 as a result of adding amino acid substitution deletion, which refers to a protein that exhibits substantially the same physiological activity as the protein having the amino acid sequence represented by SEQ ID NO: 5.

The term "F2 subunit" used in the present disclosure refers to a portion of the Newcastle disease virus fusion protein divided by a cleavage site, includes the signal sequence, and refers to a protein involved in inducing cell membranes of foreign proteins and normal folding of proteins.

In the present disclosure, the F2 subunit may include the 117th amino acid sequence from the N-terminus of the fusion protein. Specifically, the F2 subunit may be composed of the amino acid sequence represented by SEQ ID NO: 4 and includes functionally equivalent substances thereto. The term "functionally equivalent substance" refers to a substance having at least 70% or more, preferably 80% or more, more preferably 90% or more sequence homology with the amino acid sequence represented by SEQ ID NO: 4 as a result of adding amino acid substitution deletion, which refers to a protein that exhibits substantially the same physiological activity as the protein having the amino acid sequence represented by SEQ ID NO: 4.

The term "fusion peptide" used in the present disclosure refers to a protein belonging to the F1 precursor and plays a role in activating cell membrane fusion upon insertion into the target cell membrane.

In the present disclosure, the fusion peptide may be composed of the amino acid sequence represented by SEQ ID NO: 6 and includes functionally equivalent substances thereto. The term "functionally equivalent substance" refers to a substance having at least 70% or more, preferably 80% or more, more preferably 90% or more sequence homology with the amino acid sequence represented by SEQ ID NO: 6 as a result of adding amino acid substitution deletion, which refers to a protein that exhibits substantially the same physiological activity as the protein having the amino acid sequence represented by SEQ ID NO: 6.

The term "Transmembrane domain (TM)" as used in the present disclosure is a peptide composed of hydrophobic amino acids capable of stable binding to the viral envelope. It refers to a protein that allows the foreign protein to be located in the outside membrane of the viral through noncovalent bonding with the virus envelope when expressed on the cell membrane of a foreign protein.

In the present disclosure, the amino acid sequences from the 499th amino acid to the carboxyl group terminus of the Newcastle disease virus fusion protein may be used as a transmembrane domain (TM). More preferably, the amino acid sequences from 499th amino acid to 540th amino acid sequence may be used as transmembrane domain (TM). Furthermore, preferably the amino acid sequences from 499th to 530th may be used as the transmembrane domain (TM). Most preferably, the amino acid sequences from 499th to 529th may be used as the transmembrane domain (TM).

In particular, the transmembrane domain may be composed of the nucleotide sequence represented by SEQ ID NO: 7 and includes functionally equivalent substances thereto. The term "functionally equivalent substance" refers to a substance having at least 70% or more, preferably 80% or more, more preferably 90% or more sequence homology with the amino acid sequence represented by SEQ ID NO: 7 as a result of adding amino acid substitution deletion, which refers to a protein that exhibits substantially the same physiological activity as the protein having the amino acid sequence represented by SEQ ID NO: 7.

In addition, in the recombinant Newcastle disease virus, the SARS-CoV-2 spike protein RBD (receptor binding domain) and NDV surface RBD protein expression cassette may be inserted between the NP gene and the P gene of the LVP-K1 vector for insertion of a foreign gene in the order of F2-Fusion peptide-RBD-TM/CT. Preferably, the gene encoding SARS-CoV-2 RBD protein expression gene combination represented by the amino acid sequence represented by SEQ ID NO: 3 may be inserted between the NP gene and the P gene of the LVP-K1 vector for insertion of a foreign gene, represented by the nucleotide sequence represented by SEQ ID NO: 1

In addition, the SARS-CoV-2 RBD protein expression gene combination may be composed of a receptor binding domain (RBD) of SARS-CoV-2 spike protein and an NDV surface RBD protein expression cassette.

In addition, the recombinant Newcastle disease virus may further include a gene encoding a kozak sequence represented by the amino acid sequence represented by SEQ ID NO: 8. In addition, the kozak sequence may be used to increase the expression efficiency of the receptor binding domain (RBD) of the SARS-CoV-2 spike protein, which is a foreign gene.

In addition, the recombinant Newcastle disease virus may be one that expresses a receptor binding domain (RBD) of a SARS-CoV-2 spike protein on the surface of the Newcastle disease virus.

In addition, the recombinant Newcastle disease virus may be LVP-K1-RBD19 (Accession number: KCTC 14422BP) represented by the nucleotide sequence represented by SEQ ID NO: 2 and includes functionally equivalent substance thereto. The term "functionally equivalent substance" refers to a substance having at least 70% or more, preferably 80% or more, more preferably 90% or more sequence homology with the gene sequence represented by SEQ ID NO: 2 as a result of nucleotide substitution deletion, which refers to a gene or gene combination that exhibits substantially the same physiological activity as the gene sequence represented by SEQ ID NO: 2.

In addition, the present disclosure provides a vaccine composition for preventing or treating SARS-CoV-2, the composition including the recombinant Newcastle disease virus or antigen purified therefrom.

Since the vaccine composition of the present disclosure includes the above-described recombinant Newcastle disease virus, the overlapping description with the recombinant Newcastle disease virus of the present disclosure is excluded in order to avoid excessive complexity of the present specification due to the overlapping description.

In addition, the vaccine may be a live vaccine in which the virus is attenuated or an inactivated vaccine.

In addition, the inactivated vaccine may be an immunoactive product as purified LVP-K1-RBD19 recombinant NDV virus. A vaccine including the composition may be prepared by methods known in the art. For example, after obtaining purified viruses, they are treated with formalin, betapropriolactone (BPL), binary ethylenimine (BEI) or gamma rays, or inactivated by other methods known to those skilled in the art. The inactivated virus is then mixed with a pharmaceutically acceptable carrier (e.g., saline solution) and optional adjuvants. Preferably, it may be inactivated at a final concentration of 0.1% of formalin.

In addition, the vaccine composition may further include an immune enhancing material or adjuvant.

In addition, the immune enhancing material or adjuvant refers to a compound or mixture that enhances the immune response and promotes the rate of absorption after inoculation, and includes any absorption-promoting agent, but is not limited thereto. For example, it may include auxiliary molecules which are added to aluminum hydroxide, an oil such as mineral oil or a vaccine. They may include auxiliary molecules generated in the body after each induction by these additional ingredients. The auxiliary molecule includes interferon, interleukin, growth factor, and the like.

The present vaccine refers to a pharmaceutical composition containing at least one immunologically active component that induces an immunological response in a human. The immunologically active component of the vaccine is the known LVP-K1-RBD19 recombinant NDV virus. In addition, one or more additional antigens may be included to enhance the efficacy of the vaccine, and the vaccine may include one or more of the elements described above at the same time.

The vaccine may be in any form known in the art, for example, in the form of liquids and injections, or in a solid form suitable for suspension, but is not limited thereto. Such preparations may also be emulsified or encapsulated in liposomes or soluble glass, or may be produced in the form of an aerosol or spray. They may also be incorporated into transdermal patches. Liquids or injectables may contain propylene glycol if necessary and sodium chloride in an amount sufficient to prevent hemolysis (e.g., about 1%).

The vaccine of the present disclosure may further include a pharmaceutically acceptable carrier or diluent. In the above description, "pharmaceutically acceptable" refers to a non-toxic composition that is physiologically acceptable, does not inhibit the action of the active ingredient when administered to humans and does not normally cause allergic reactions such as gastrointestinal disorders, dizziness, or similar reactions.

Suitable carriers for vaccines are known to those skilled in the art and include proteins, sugars, and the like, but are not limited thereto. Such carriers may be aqueous or non-aqueous solutions, suspensions or emulsions. Regular or atypical organic or inorganic polymers may be used as an adjuvant for increasing immunogenicity. Adjuvants are generally known to promote immune responses through chemical and physical binding to antigens. For example, an atypical aluminum gel, an oil emulsion, or a double oil emulsion and an immunosol may be used as an adjuvant. In addition, various plant-derived saponins, Levamisole, CpG dinucleotide, RNA, DNA, LPS, various types of cytokines, etc. may be used to promote an immune response. The above immune composition can be used as a composition for inducing an optimal immune response by a combination of various adjuvants and immune response promoting additives. In addition, stabilizers, inactivating agents, antibiotics, preservatives, and the like may be used as the composition to be added to the vaccine. The vaccine antigen may be mixed with distilled water or a buffer solution depending on the route of administration of the vaccine.

The vaccine may be administered via oral, intramuscular, subcutaneous route, or the like, but is not limited thereto, and may be preferably administered via an intramuscular route.

In addition, the present disclosure provides a method of preventing or treating SARS-CoV-2 infection, the method including administering the vaccine composition to an individual.

The method of the present disclosure includes the above-described vaccine composition. Thus, descriptions of the contents overlapping with the above-described vaccine composition of the present disclosure are excluded in order to avoid excessive complexity of the present specification due to the description of overlapping contents.

The "individual" of the present disclosure refers to a subject in need of a method for preventing, adjusting or treating a disease, and more specifically, a human or non-human primate, mouse, rat, dog, cat, horse, cattle, and other mammals.

The "prevention" of the present disclosure refers to any action that suppresses or delays the onset of SARS-CoV-2 infection by administration of the composition according to the present disclosure.

The "treatment" of the present disclosure refers to any action that improves or changes advantageously the symptoms of SARS-CoV-2 infection by administration of the composition according to the present disclosure.

Further, the present disclosure provides the method of preparing the recombinant Newcastle disease virus, the method including the steps of inoculating a host cell line with the recombinant Newcastle disease virus; culturing the host cell line; and obtaining a recombinant Newcastle disease virus from the culture of the host cell line.

In the present disclosure, the recombinant virus LVP-K1-RBD19 may be recovered through a conventional virus construction method. After infectious clone cDNA represented by SEQ ID NO: 2 for SARS-CoV-2 RBD protein expression is completely constructed, three types of helper plasmids (NP, P, L) and modified vaccina virus (MVA/T7) are injected into the HEp-2 cell line. After culturing, the procedure for recovering the recombinant virus is carried out according to a conventional method. Transfection is performed using lipofectamine 3,000 as the injection method into the cell line, and HEp-2 cells are used as the cell line. After culturing for three to four days, the recombinant virus is recovered and inoculated into the allantoic cavity of an 8th to 10th day-old SPF fertilized egg. After culturing the virus, the allantoic fluid is recovered. In the same way, blind passages were performed through culture on fertilized eggs for at least two passages to increase the virus titer. Then, allantoic fluid is purified by a conventional purification method. Then, they are cultured in the Vero 76 cell line selected as an appropriate cell line. The obtained cells are used for the experiment. In order to confirm the viral surface expression of the SARS-CoV-2 RBD protein on the recombinant virus line LVP-K1-RBD19, the reverse transcription PCR method is used to confirm the gene stability and mRNA expression of the RBD protein, and Western blotting is used to confirm the RBD expression. The virus purification is performed for confirmation.

After harvesting the recombinant virus culture solution, centrifugation is performed for clarification. Clarification can be performed by centrifugation or microfiltration. The centrifugation is performed in a condition of 10,000 g, 10 minutes, and 4° C. Supernatants can be used for the next purification process. In the case of microfiltration, a filter with a pore size of 1.0 μm to 0.2 μm can be used, and a 0.45 μm pore size filter can be used preferably. As the filtration method, either dead end filtration or cross flow filtration can be used, and both methods are applicable. Recombinant virus purification can be performed by known methods, including extraction through chromatography or ultrafiltration methods. In the purification method using chromatography, virus purification may be performed by the combination of an appropriate resin and buffer through affinity, ion exchange, exclusion according to size, and differences in binding strength such as hydrophobicity. In general, virus purification is performed in which the virus is recovered by precipitating or separating the virus by ultra-high-speed centrifugation using sucrose gradient media, and the recovered virus is resuspended in TNE buffer for use in the next process. The LVP-K1-RBD19 recombinant virus is purified using a cation exchange resin chromatography method, and the fraction extracted at a specific concentration is recovered through a sodium chloride concentration gradient after sample loading. The virus is recovered by precipitating or separating the virus by ultra-high-speed centrifugation using sucrose gradient media on the recovered fraction, and the recovered virus is resuspended in physiological saline for injection and used in the next process.

In addition, the present disclosure provides a method of inducing a protective immune response against SARS-CoV-2 in a human, the method including administering an effective immune amount of the vaccine composition to the human.

In addition, the vaccine composition may include a live vaccine composition.

In addition, the immune response shows production or activation of an antibody, B cells, helper T cells, suppressor T cells, cytotoxic T cells and gamma-delta T cells specifically directed against an antigen or antigens contained in the vaccine composition or vaccine including the same, a therapeutic or protective immunological response in the host so as to include one or more effects of enhancing resistance to new infections or reducing the clinical severity of the disease, but is not limited thereto. Preferably, it may be a protective immune response.

In addition, the protection is evidenced by a reduction or absence of clinical signs normally exhibited by an infected host, a faster recovery time or a lower duration, or a lower viral titer in the tissues or body fluids or feces of the infected host.

In addition, the effective immune amount refers to an amount of a vaccine capable of inducing an immune response to reduce the frequency or severity of SARS-CoV-2 infection in humans, and those skilled in the art can appropriately select it. For example, if a vaccine includes the vaccine composition, the effective immune amount of purified virus may be $10^{5.0}$ $TCID_{50}$/ml to $10^{8.0}$ $TCID_{50}$/ml. More preferably, it may be $10^{6.0}$ $TCID_{50}$/ml to $10^{7.0}$ $TCID_{50}$/ml or more.

The immune response induction method is not limited thereto, but may be inoculating the vaccine composition by oral, transdermal, intramuscular, intraperitoneal, intravenous, or subcutaneous routes. Preferably, the vaccine may be intramuscularly inoculated upon the first and second inoculations.

Finally, the present disclosure provides a method for evaluating an immune response in an animal, the method including administering a recombinant Newcastle disease virus to the animal.

In addition, the method may be to measure and evaluate an IgG antibody titer from animal serum.

The animal is preferably a mammal, and the present disclosure includes immunogenicity evaluation in mice. The inoculation may be performed within two times at a predetermined time interval through the intramuscular, subcutaneous, oral route, or nasal skin of the immunized animal, and preferably, the inoculation may be performed twice at an interval of two weeks through intramuscular inoculation. Two weeks after immunization of the immunized animal, mouse serum is obtained through tail blood collection or orbital blood collection. The IgG antibody titer is measured by an ELISA system to confirm the effect on immune induction. Preferably, the protective antibody titer can be measured by measuring the virus neutralization antibody titer for suppressing viral infection.

In addition, the present disclosure includes a method for measuring neutralizing antibody titers to SARS-CoV-2. An HIV-1-based SARS-CoV-2 spike protein expression pseudovirus (HIV-2019-nCoV-spikepps-myc-Luc) is constructed to measure the luciferase activity by the virus-neutralizing antibody. Thus, the method for indirectly measuring the neutralizing antibody titer is provided. The virus neutralizing antibody titer of the vaccine tested in the present disclosure through the above method may be 12 to 512 folds, preferably 128 to 256 folds, and more preferably 256 folds or more.

Hereinafter, the present disclosure is described in more detail through examples. These examples are for explaining the present disclosure in more detail, and the scope of the present disclosure is not limited to these examples.

Example 1. Preparation of Recombinant NDV Virus Genome Transcription Vector Using NDV VG/GA Strain as a Basic Backbone NDV VG/GA (Gene bank No. KC906188.1) has a negative-sense single-stranded RNA of about 15 kb as genetic information and is composed of six ORFs, and the proteins constituting the structure of the virus encodes NP, P, M, F, HN and L genes. After RNA isolation using a viral RNA extraction kit (Qiagen), four pairs of primers specific for the gene were prepared, and reverse transcription polymerase chain reaction (RT-PCR) was performed. Four pairs of primers specific for the gene are shown in Table 1. RT-PCR was performed by reaction at 42° C. for 1 hour and at 94° C. for 5 minutes, followed by a total of 30 cycles of 94° C. for 1 minute, 60° C. for 1 minute, and 72° C. for 1 minute, followed by reaction at 72° C. for 7 minutes. A cloning strategy for serially ligating a set of four cDNA fragments is shown in FIG. 1A. In order to increase the reconstruction efficiency of the vector, preferably the modified pBR322 vector, a low-copy-number plasmid, was used for cloning by locating PacI and PmeI restriction enzymes having different recognition sites and cleavage sites. The modified pBR322 vector was preferably under the control of the T7 RNA polymerase promoter and was positioned so that it is terminated by the hepatitis delta virus (HDV) antigenome ribozyme and T7 terminator gene used to split RNA at the terminus of the NDV genome, thereby allowing viral encapsulation and packaging. In addition, the complete genome sequence of the NDV VG/GA strain was included to ensure accurate transcription. Then, as shown in Table 2 below, a cloning strategy was used in which the cDNA fragment set was divided into four pieces and successively ligated (see FIGS. 1B and 1C).

RNA-dependent RNA polymerase initiates transcription in a sequential manner by a stop-start mechanism between genes (GE-IG-GS). In GS, the transcriptional re-initiation was incomplete, so the level of transcription of mRNA located at the 3' terminus was high. Therefore, as it goes toward the 3' terminus, the level of the mRNA transcription is higher, but as it goes toward the 5' terminus, the level is lower. Therefore, the new foreign gene insertion between the NP gene and the P gene may be more preferable than between the P gene and the M gene and between the HN gene and the L gene, since higher levels of mRNA transcription and foreign protein translation occur.

The four cDNA fragments have the same nucleotide sequence at the terminus of 15 bp, and a transgene cassette consisting of an IGS (GE-IG-GS) sequence and MCS (multicloning site) was inserted between the NP gene and P gene by overlap cloning to construct the LVP-K1 vector for foreign gene insertion.

TABLE 1

| Gene | | Direction | Sequence (5'→3') | Restriction site |
|---|---|---|---|---|
| Fragment 1 (L2) | SEQ ID NO: 9 | Forward | ACGCGTggtctcaggtttatatgcagggaa | MluI |
| | SEQ ID NO: 10 | Reverse | TTAATTAAaccaaacaaagatttggtgaatg | PacI |
| Fragment 2 (L1) | SEQ ID NO: 11 | Forward | ACTAGTtgagattctcaaggatgatggggt | SpeI |
| | SEQ ID NO: 12 | Reverse | ACGCGTcgagtgcaagagactaatagtttt | MluI |
| Fragment 3 (F-HN) | SEQ ID NO: 13 | Forward | GGCGCCattatcggtggtgtagctctcgg | Kas I |
| | SEQ ID NO: 14 | Reverse | ACTAGTaaagggacgattctgaattccccg | SpeI |
| Fragment 4 (P-M-F) | SEQ ID NO: 15 | Forward | CCGCGGaaacagccaagagagaccgcagaa | SacII |
| | SEQ ID NO: 16 | Reverse | GGCGCCaaccgggatccagaatcttctacccgt | Kas I |

TABLE 1 -continued

| Gene | | Direction | Sequence (5'→3') | Restriction site |
|---|---|---|---|---|
| Fragment 5 (NP-P) | SEQ ID NO: 17 | Forward | GTTTAAACaccaaacagagaatccgtaagg | PmeI |
| | SEQ ID NO: 18 | Reverse | CCGCGGctttgttgactccctgttgttga | SacII |

TABLE 2

| Gene | | Direction | Sequence (5'→3') | Size (bp) |
|---|---|---|---|---|
| Fragment 1 (pBR322-NP) | SEQ ID NO: 19 | Forward | TTCTCGCTTCCGGCGGCATC | 5,036 |
| | SEQ ID NO: 20 | Reverse | CCGCTTCTACCCGTATTTTTTCTAAGCAGAGGAATTGGGATGACCTC | |
| Fragment 2 (P-M) | SEQ ID NO: 21 | Forward | TACGGGTAGAAGCGGCCGCGGCCGGCCCCACACCCCACCCCTCAATCC | 2,938 |
| | SEQ ID NO: 22 | Reverse | CCGGGATCCAGAATCTTCTACCC | |
| Fragment 3 (F-HN) | SEQ ID NO: 23 | Forward | GATTCTGGATCCCGGTTGGCG | 5,578 |
| | SEQ ID NO: 24 | Reverse | CCGCCATCACTTGACAGTTCC | |
| Fragment 4 (L) | SEQ ID NO: 25 | Forward | GTCAAGTGATGGCGGAAGGG | 5,256 |
| | SEQ ID NO: 26 | Reverse | CGCCGGAAGCGAGAAGAATC | |

Example 2. Construction of Recombinant NDV Virus cDNA of which SARS-CoV-2 RBD Protein is Expressed on Surface A recombinant Newcastle disease virus (NDV) expressing the receptor binding domain (RBD) of the SARS-CoV-2 spike protein on the surface was constructed.

First, the gene encoding RBD protein (SEQ ID NO: 3) was inserted into the NDV surface expression cassette (genes encoding the F2 subunit (including signal sequence and HR4), fusion peptide, transmembrane domain and cytoplasmic tail of the Newcastle disease virus fusion protein) for surface expression of Newcastle disease virus (NDV) to construct a SARS-CoV-2 RBD protein expression gene combination (see FIG. 2). The SARS-CoV-2 RBD protein expression gene combination was designed and synthesized to have a FseI restriction enzyme recognition site and a kozak sequence (SEQ ID NO: 8) at the N terminus, and a FseI restriction enzyme recognition site at the C terminus and to be inserted between the NP gene and the P gene of Newcastle disease virus.

Then, the LVP-K1 vector for foreign gene insertion of Example 1 and the SARS-CoV-2 RBD protein expression gene combination, respectively were treated with FseI restriction enzyme, and then purified using PCR purification and Gel purification kit. After calculating the LVP-K1 vector for foreign gene insertion and the RBD expression cassette in a ratio of 1:3, ligation was performed overnight at 4° C. using T4 ligase, and the transformation was performed with E. coli TOP10 competent cells using a furnace heat shock method (heat shock). Then, the seeds were determined through colony PCR. The plasmid midi preparation was used to obtain a plasmid expressing the RBD of the SARS-CoV-2 spike protein on the surface of the Newcastle disease virus, and recombinant Newcastle disease virus LVP-K1-RBD19 (Accession number: KCTC 14422BP) was produced.

Example 3. Construction of Recombinant Newcastle Disease Virus LVP-K1-RBD19

Figures 3A, 3B:
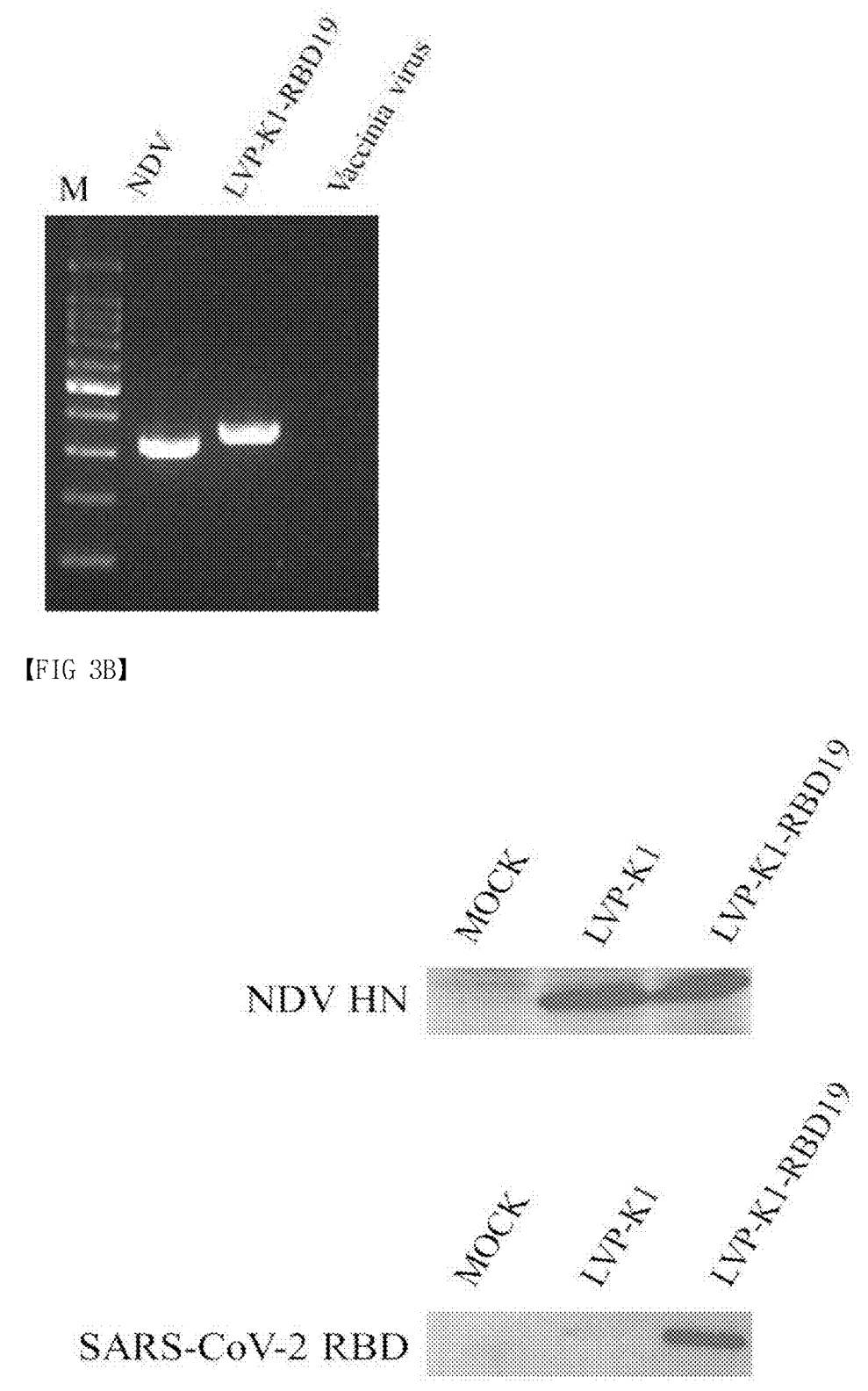

Individual clones (NP, P, L) of the NDV transcriptase complex were cloned into pBR322 vector and used as helper plasmids (pBR322-NP, pBR322-P, pBR322-L). HEp-2 cells were prepared at $5 \times 10^5$ cells/well in a 6-well plate the day before. Then, the modified vaccinia virus (MVA-T7) was infected with 1 MOI (multiplicity of infection). 2.5 μg, 1.5 μg, 0.5 μg, and 5 μg of pBR322-NP, pBR322-P, and pBR322-L Helper plasmids expressing proteins by the T7 promoter and LVP-K1-RBD19, a plasmid expressing RBD of SARS-CoV-2 spike protein on the surface were mixed with Lipofectamine 3000 (Invitrogen) at an appropriate ratio in the cell line to perform their transfection. Thereafter, the HEp-2 cell supernatant was harvested after incubation at conditions of 37° C. and 5% $CO_2$ for three to four days. Then, they were inoculated into the allantoic cavity of 9th to 11th days old SPF embryonated egg. The allantoic fluid was collected four days after inoculation. To remove vaccinia virus, allantoic fluid diluted at $10^{-3}$ with PBS was inoculated into the allantoic cavity of the 9th to 11th days old SPF embryonated egg. The allantoic fluid was collected four days after inoculation to conduct a virus confirmation experiment. The virus confirmation experiment was performed as follows. The allantoic fluid was isolated using a Viral RNA extraction kit (Qiagen). 5 μl of extracted RNA and 1 μl of each of Forward and Reverse primers in Table 3 below were used to react at 42° C. for 1 hour, at 94° C. for 5 minutes, then perform a total of 35 cycles of at 94° C. for 1 minute, at 60° C. for 1 minute, and at 72° C. for 1 minute, and then react at 72° C. for 7 minutes by ONE-STEP RT-PCR. The results are shown in FIG. 3A.

As shown in FIG. 3A, it was confirmed that the vaccinia virus was removed, and only Newcastle disease virus and recombinant Newcastle disease virus LVP-K1-RBD19 (SEQ ID NO: 2) remained.

TABLE 3

| Gene | | Direction | Sequence (5'→3') | Size (bp) |
|---|---|---|---|---|
| NDV check | SEQ ID NO: 27 | Forward | CCACAATTCCAAGATAACCGGAG | 327 |
| | SEQ ID NO: 28 | Reverse | GCTGCCACAATCAGATGCCTTTG | |
| RBD check | SEQ ID NO: 29 | Forward | GTCAGACAAATCGCTCCAGGG | 363 |
| | SEQ ID NO: 30 | Reverse | AGGTCCACAAACAGTTGCTGG | |
| Vaccinia virus check | SEQ ID NO: 31 | Forward | ATGACGATGAAAATGATGGTACATA | 1,059 |
| | SEQ ID NO: 32 | Reverse | CTCCAATACTACTGTAGTTGTAAGG | |

Example 4. Culture and Purification of Recombinant Newcastle Disease Virus LVP-K1-RBD19

Vero 76 cells were cultured at $3\times10^5$ cells/mL. On the next day, the recombinant virus was inoculated at 0.05 MOI (multiplicity of infection). The virus supernatant having the highest titer was obtained two days after inoculation. Thereafter, the virus supernatant was centrifuged at 5,000 g, 4° C. for 10 minutes to remove suspended solids, and the supernatant was collected. The collected supernatant was ultracentrifuged at 32,000 rpm at 4° C. for 3 hours to concentrate the recombinant virus. After removing the supernatant, they were resuspended in TNE buffer (10 mM Tris-HCl, 20 mM NaCl, 1 mM EDTA). The concentrated virus was ultracentrifuged at 32,000 rpm and 4° C. for 2 hours using a 30-60% sucrose gradient method. Recombinant virus was obtained in 40-50%. Finally, the obtained recombinant virus was ultracentrifuged once more at 32,000 rpm at 4° C. for 2 hours to remove sucrose, thereby purifying the recombinant Newcastle disease virus LVP-K1-RBD19.

Example 5. Confirmation of RBD Surface Expression

Receptor binding domain (RBD) expression of SARS-CoV-2 spike protein of the recombinant virus purified in Example 4 was confirmed. First, BCA protein analysis was used to measure the protein concentration. Then, 20 μg of protein was separated through 10% SDS-PAGE and electrophoresed (transferred) on a PVDF membrane. In the membrane, protein expression using SARS coronavirus spike protein olyclonal antibody (Invitrogen) and NDV HN protein polyclonal antibody (Bioss) was confirmed. The results are shown in FIG. 3B. As shown in FIG. 3B, the recombinant SARS-CoV-2 RBD protein of about 42 kDa and about 68 kDa, respectively, was confirmed. In addition, in LVP-K1 confirmed as the positive control, the target band was not detected in the SARS coronavirus spike protein polyclonal antibody, and the band was confirmed only in the NDV HN protein polyclonal antibody. Thus, it can be seen that RBD protein was not detected in LVP-K1.

Example 6. Inactivation of Recombinant Newcastle Disease Virus LVP-K1-RBD19

Partial samples of the virus purified in Example 4 were taken, and virus titers were measured using Vero 76 cells. The virus titer was measured according to the general $TCID_{50}$ measurement method, and the titer was adjusted using PBS according to the virus titer. After diluting the virus titer to $10^{8.0}$ $TCID_{50}$/ml, 0.1% aqueous formalin was added thereto. They were stored at 4° C. for 48 hours. After inactivation, samples were collected at 6-, 12-, 24-, 36-, and 48-hours using Vero 76 cells. To observe CPE caused by virus infection, the titer was observed using the $TCID_{50}$ method for five days to confirm inactivation. As a result of the inactivation experiment, it was confirmed that the infective activity of all viruses disappeared within 24 hours. As shown in FIG. 4, the viral antigen used in the additional experiment was inactivated for 24 hours at a final concentration of 0.1% formalin.

Example 7. Sandwich Enzyme-Linked Immunosorbent Assay (ELISA) for Measuring RBD Protein Surface Expression of Recombinant Newcastle Disease Virus LVP-K1-RBD19

In order to determine the relative amount of antigen, the level of RBD protein expression on the viral surface was confirmed using a sandwich ELISA. The permissible concentrations of the coating antibody and the detecting antibody were confirmed by the checkerboard method. Sandwich ELISA was performed as follows. SARS-CoV-2 spike protein polyclonal antibody (Invitrogen) was diluted to a concentration of 1:1000 in carbonate-bicarbonate buffer (40 mmol/L $Na_2CO_3$, 60 mmol/L $NaHCO_3$, pH9.6). Then, a 96-well plate was coated with the coating buffer at 4° C. In next day, the coating buffer was discarded, and the plate was blocked using 1% BSA diluted in PBS. The inactivated virus ($10^{6.7}$ $TCID_{50}$/mL) was serially diluted 10-fold using PBS. 100 μl/well of the virus sample was added and incubated at 37° C. for 1 hour. Anti-SARS-CoV-2 spike RBD antibody (MAB10540-SP, 1 μg/mL) diluted in PBS at 1:1,000 after washing five times with PBST (PBS containing 0.5% Tween20) was treated at 100 μl/well at 37° C. for one hour. After washing with PBST five times, an anti-mouse IgG secondary antibody labeled with horseradish peroxidase (HRP) was treated at 1:5,000 at 37° C. for one hour according to the manufacturer's instructions. The TMB substrate solution was treated at 100 μl/well and then cultured at room temperature for 30 minutes in the dark. The reaction was stopped by adding 50 μl/well of 2M $H_2SO_4$. In the present disclosure, purified RBD protein (R&D system) was used as a positive control. Optical density (OD) was measured at 450 nm using a microplate reader (iMark, Bio-Rad). The result indicates that the protein expression amount of $10^{7.7}$ $TCID_{50}$/mL LVP-K1-RBD19 was about 10 μg/mL.

Example 8. Confirmation of Immunogenicity of Recombinant Newcastle Disease Virus LVP-K1-RBD19

In recombinant Newcastle disease virus LVP-K1-RBD19, an RBD (receptor binding domain) of SARS-CoV-2 spike protein is expressed on the surface. In order to confirm the production effect of antibody against RBD as an antigen of RBD, 7-week-old, female BALB/c mice were vaccinated with LVP-K1-RBD19 as follows. Specifically, four groups included the PBS inoculation group, the LVP-K1 inactivated virus $10^{7.0}$ $TCID_{50}$/dose inoculation group, the LVP-K1-RBD19 inactivated virus $10^{6.0}$ $TCID_{50}$/dose inoculation group, and $10^{7.0}$ $TCID_{50}$/dose inoculation group. Five animals in each group were vaccinated. The intramuscular inoculation was performed twice at an interval of 2 weeks at an amount of 100 μl/animal. From the first inoculation date, antisera were prepared through orbital blood sampling before vaccination, 2 weeks after vaccine inoculation (at the time of the second vaccine inoculation), and 3 and 4 weeks after vaccine inoculation. Then, in order to confirm the antibody reaction between the antisera and the RBD protein, ELISA antibody measurement was performed. In order to measure the antibody titer against SARS-CoV-2 RBD protein by LVP-K1-RBD19 antigen, a 96-well plate for ELISA measurement was coated with 100 μl per well using 2.5 μg/mL of recombinant RBD protein expressed using recombinant CHO cells, and serum diluted 100 times with PBS was used to measure the antibody titer according to a general ELISA measurement method. The results are shown in FIG. 6A.

Figures 5B, 6A:
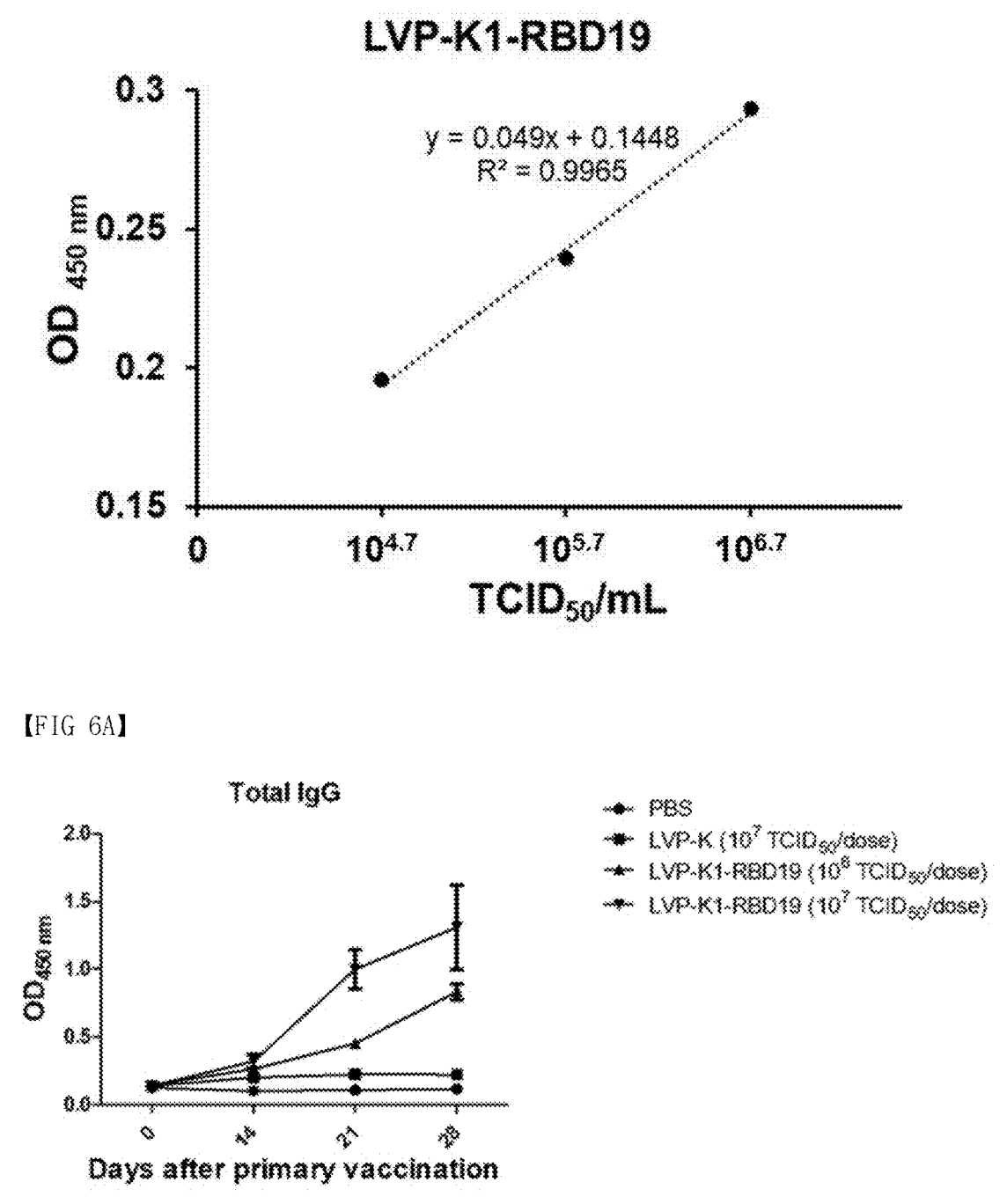
Figures 6B, 7A:
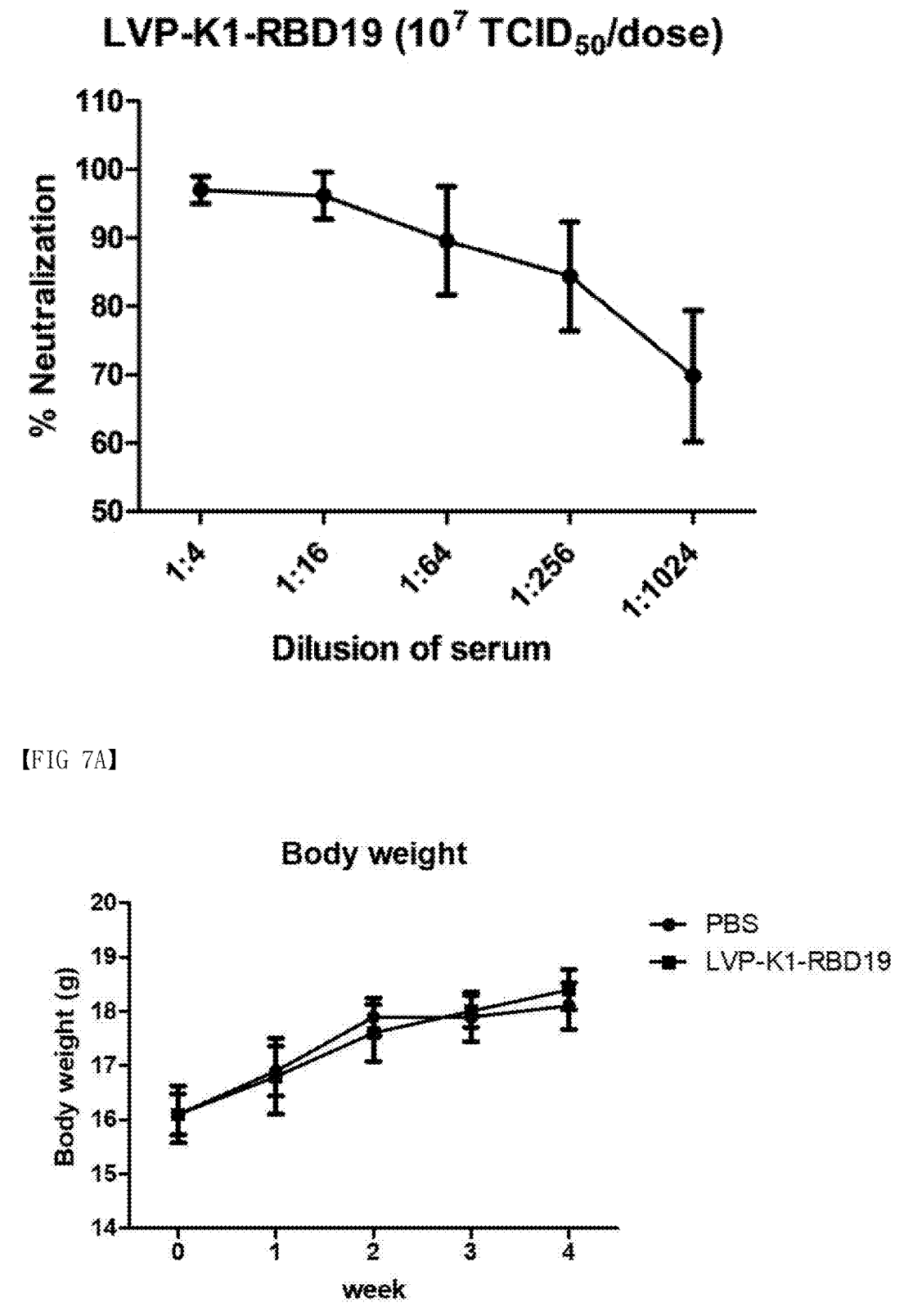

As shown in FIG. 6A, it was confirmed that the total IgG antibody titer to RBD protein of the group inoculated with the LVP-K1-RBD19 antigen showed a significant difference from the control group, and compared to the LVP-K1 antigen inoculation group, the antibody titer of $10^{6.0}$ $TCID_{50}$/dose inoculation group was quite high and the antibody titer of $10^{7.0}$ $TCID_{50}$/dose antigen concentration was further increased. Through these results, it was confirmed that the IgG antibody to the SARS-CoV-2 RBD protein was effectively formed through the LVP-K1-RBD19 virus antigen.

Example 9. Evaluation of Neutralizing Antibody Titer Against RBD Protein of Recombinant Newcastle Disease Virus LVP-K1-RBD19

A neutralizing antibody induction test by the LVP-K1-RBD19 virus antigen obtained in Example 8 was performed. The neutralizing antibody titer test was performed using a pseudovirus (HIV-2019-nCoV-spike pps-myc-Luc). Specifically, the serum obtained in Example 7 was diluted in a 96-well plate by binary dilution, and then the same amount of pseudovirus (virus titer: $1\times10^{3.0}$ $TCID_{50}$/ml) was added and reacted at room temperature for one hour. After completion of the reaction, they were transferred to a pre-prepared 96-well plate with a monolayer-formed Huh7 cell, followed by a reaction for one hour. After completion of the reaction, the mixed solution with the virus and serum was removed. Then, they were washed once with a cell culture medium that does not contain FBS. Then, the cell culture medium was added, and they were cultured in a $CO_2$ incubator at 37° C. for 18 hours. For the luciferase assay, fluorescence (Fluc) emitted from cells was measured using the bright Glo luciferase assay system (Promega). After discarding the medium, 50 μl of luciferase lysis buffer was added to each well, and then stored frozen at −70° C. for 24 hours. Then, a luciferase reagent was added to measure the relative light unit (RLU). RLU was measured using a GLOMAX luminometer, and the change to the virus neutralizing antibody titer was calculated according to the formula in Equation 1 below, and the median neutralization dose was calculated by the Reed-Munch method.

$$\text{Neutralization (\%)} = \frac{RLU \text{ without serum} - RLU \text{ with serum}}{RLU \text{ without serum}} \times 100 \quad \text{[Equation 1]}$$

Example 10. Toxicity and Safety Evaluation of Antigen

For antigen toxicity and safety evaluation, 50 μl of PBS with $2.0\times10^{7.0}$ $TCID_{50}$ of LVP-K1-RBD19 antigen was inoculated twice at 2-week intervals in the femoral muscle of C57BL/6 mice. Then, body weight change, feed intake and water intake were measured for 4 weeks. The negative control group was inoculated with the same amount of PBS. Ten mice per each test group were performed. The results are shown in FIG. 7.

As shown in FIG. 7, it was confirmed that there was no significant difference in body weight change, feed intake and water intake between the PBS inoculation group and the antigen inoculation group. These results mean that the LVP-K1-RBD19 virus antigen is non-toxic and has excellent safety, so it is suitable for use as a vaccine for the prevention and treatment of SARS-CoV-2.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

[Certificate of Deposit of Microorganisms]

Name of deposit institution: Korea Research Institute of Bioscience and Biotechnology Korean Collection for Type Center (KCTC) (the address: 181, Ipsin-gil, Jeongeup-si, Jeollabuk-do, 56212, Republic of Korea)

Accession number: KCTC 14422BP

Deposit date: Dec. 29, 2020

What is claimed is:

1. A vector for insertion of a foreign gene, comprising Newcastle disease virus cDNA including genes encoding NP, P, M, F, HN and L proteins and a transgene cassette, wherein the transgene cassette includes a sequence of Gene start (GS)-Intergenic sequence (IG)-Gene end (GE)) and MCS (multicloning site), wherein the vector is SEQ ID NO: 1.

2. The vector of claim 1, wherein the transgene cassette is inserted between an NP gene and a P gene of the Newcastle disease virus.

3. A recombinant Newcastle disease virus comprising the vector of claim 1 and a gene encoding a receptor binding domain (RBD) of SARS-CoV-2 spike protein.

4. The recombinant Newcastle disease virus of claim 3, wherein the recombinant Newcastle disease virus further includes an NDV surface expression cassette,
wherein the NDV surface expression cassette includes genes encoding F2 subunit, fusion peptide, transmembrane domain and cytoplasmic tail of Newcastle disease virus fusion protein, and
wherein the F2 subunit includes signal sequence.

5. A vaccine composition for preventing or treating SARS coronavirus (SARS-CoV-2), the vaccine composition comprising (i) the recombinant Newcastle disease virus of claim 4 or (ii) antigen purified from the virus, and an adjuvant.

6. The recombinant Newcastle disease virus of claim 3, wherein the recombinant Newcastle disease virus further includes a gene encoding a kozak sequence of SEQ ID NO: 8.

7. A vaccine composition for preventing or treating SARS coronavirus (SARS-CoV-2), the vaccine composition comprising (i) the recombinant Newcastle disease virus of claim 6 or (ii) antigen purified from the virus, and an adjuvant.

8. The recombinant Newcastle disease virus of claim 3, wherein the recombinant Newcastle disease virus expresses the receptor binding domain (RBD) of the SARS-CoV-2 spike protein on a surface of the Newcastle disease virus.

9. A vaccine composition for preventing or treating SARS coronavirus (SARS-CoV-2), the vaccine composition comprising (i) the recombinant Newcastle disease virus of claim 8 or (ii) antigen purified from the virus, and an adjuvant.

10. The recombinant Newcastle disease virus of claim 3, wherein the recombinant Newcastle disease virus is LVP-K1-RBD19 (Accession Number KCTC 14422BP).

11. A vaccine composition for preventing or treating SARS coronavirus (SARS-CoV-2), the vaccine composition comprising (i) the recombinant Newcastle disease virus of claim 10 or (ii) antigen purified from the virus, and an adjuvant.

12. A vaccine composition for preventing or treating SARS coronavirus (SARS-CoV-2), the vaccine composition comprising (i) the recombinant Newcastle disease virus of claim 3 or (ii) antigen purified from the virus, and an adjuvant.

13. The vaccine composition of claim 12, wherein the vaccine is a live vaccine in which the virus is an attenuated vaccine or an inactivated vaccine.

14. The vaccine composition of claim 12, wherein the vaccine composition further includes an immune enhancing material.

15. A method of preventing or treating a SARS coronavirus (SARS-CoV-2) infection, comprising administering the vaccine composition of claim 12 to a subject in need thereof.

16. A method of producing a recombinant Newcastle disease virus, the method comprising:
inoculating a host cell line with the recombinant Newcastle disease virus of claim 3;
culturing the host cell line; and
obtaining a recombinant Newcastle disease virus from a culture of the host cell line.

17. A method of evaluating an immune response in an animal, comprising administering the recombinant Newcastle disease virus of claim 3 to the animal.

18. The method of claim 17, wherein the method is to measure and evaluate an IgG antibody titer from a serum of the animal.

19. The recombinant Newcastle disease virus of claim 3, wherein the recombinant Newcastle disease virus has a nucleotide sequence of SEQ ID NO: 2.

* * * * *

SEQUENCE LISTING

```
<160> NUMBER OF SEQ ID NOS: 32

<210> SEQ ID NO 1
<211> LENGTH: 19091
<212> TYPE: DNA
<213> ORGANISM: Artificial Sequence
<220> FEATURE:
<223> OTHER INFORMATION: LVP-K1 vector

<400> SEQUENCE: 1
```

| | |
|---|---|
| accaaacaga gaatccgtaa ggtacgatag aaggcgaagg agcaatcgaa gtcgtacggg | 60 |
| tagaaggtgt gaatctcgag tgcgagcccg aagctcaaac tcgagagagc cttctgccaa | 120 |
| aatgtcttct gtattcgatg agtacgagca gctcctcgcg gctcagactc gccccaatgg | 180 |
| agctcatggc ggaggagaga aggggagcac cttaaaggta gaagtcccgg tattcactct | 240 |
| caacagtgat gacccagaag atagatggaa cttttgcagtg ttttgtcttc ggattgctgt | 300 |
| tagcgaggat gccaacaaac cacttaggca aggtgctctc atatctctct tatgttccca | 360 |
| ctctcaagtg atgaggaacc atgttgccct tgcggggaaa cagaatgagg ccacactggc | 420 |
| tgttcttgag atcgatggtt ttaccaacgg cgtgccccag ttcaacaaca ggagtggagt | 480 |
| gtctgaagag agagcacaga gatttatgat gatagcaggg tctctccctc gggcatgcag | 540 |
| caacggtacc ccgttcgtca cagctggggt tgaagatgat gcaccagaag acattactga | 600 |
| taccctggag aggatcctct ctatccaggc tcaagtatgg gtcacggtgg caaaggccat | 660 |
| gactgcatat gagacagcag atgagtcaga aacaagaaga atcaataagt acatgcagca | 720 |
| aggcagggtc cagaagaagt acatcctcca ccccgtatgc aggagcgcaa tccaactcac | 780 |
| aatcagacag tctctggcgg tccgcatctt tttggttagc gagcttaaga gaggccgcaa | 840 |
| cacggcaggt gggacctcca cctattacaa cttggtgggg gatgtagact catacatcag | 900 |
| gaacactggg ctaactgcat tcttcctgac acttaaatat ggaattaaca ccaagacatc | 960 |
| agcccttgca cttagcagcc tctcaggcga tatccagaaa atgaagcagc tcatgcgctt | 1020 |
| gtatcggatg aaaggagata atgcgccgta catgacattg ctcggtgaca gtgaccagat | 1080 |
| gagctttgca cctgccgagt atgcacaact ttactccttt gccatgggta tggcatcagt | 1140 |
| cctagataaa ggaactagca ataccaatt tgccagggac tttatgagca catcattctg | 1200 |
| gagacttgga gtagagtacg ctcaggctca aggaagtagc atcaatgagg atatggccgc | 1260 |
| cgagctaaag ctaaccccag cagcaaggag aggcctggca gctgctgccc aaagagtgtc | 1320 |
| tgaggagacc agcagcatgg acatgcccac ccaacaagcc ggggtcctca ctggactcag | 1380 |
| cgacggaggc tcccaagccc cccaaggtgc actgaacaga tcacaaggcc aaccggacac | 1440 |
| cggggatggg gagacccaat ttctggatct gatgagagcg gtggcaaata gcatgagaga | 1500 |
| agcgccaaac tctgcgcagg gcaccccctca accggggcct cccccaaccc ctgggccctc | 1560 |
| tcaagacaat gacaccgact gggggtactg accgacagca cccagtttgc ttctatgagg | 1620 |
| tcatcccaat tcctctgctt agaaaaaata cgggtagaag cggccgcggc cggccccaca | 1680 |
| ccccacccct caatccgcaa tcccgcatgg ccaaacccac aaacgaaccc ccctgtctcc | 1740 |
| ctcctctccc ccagccccac aaccccacct gcccagggca acataggtac aatgcgaccc | 1800 |
| actaataatc aatacagggc caaagaaatt agaaaaaagt acgggtagaa gggagacatt | 1860 |
| cagagatcag ggcgagtcac ccgggtctct gctctccctt ctacctagtg gattaggatg | 1920 |
| gagatggcca cctttacaga tgcggagatc gacgagctat ttgagaccag tggaactgtc | 1980 |
| attgacagca taattacggc ccagggaaaa ccagtagaga ctgttggaag gagtgcaatc | 2040 |
| ccacaaggca aaactaaggc tttgagcgca gcatgggaga agcatgggag catccagtca | 2100 |
| ccagccagcc aagacacccc tgatcgacag gacagatcag ataaacaact gtccacaccc | 2160 |
| gagcaagcga gtccaaacga cagcccccca gccacatcca ctgaccagcc tcccactcag | 2220 |
| gctgcagatg aggccggcga tacacagctc aagaccggag caagcaactc tctgctgtcg | 2280 |
| atgcttgata aactcagcaa taagtcatct aatgctaaaa agggcccagg gtcgagccct | 2340 |

```
caagaaaggc atcatcaacg tctgactcaa aacaggggga gtcaacaaag ccgcggaaac    2400
agccaagaga gaccgcagaa ccaggccaag gccatccctg gaaaccaggt cacagacgcg    2460
aacacagcat atcatggaca atgggaggag tcacaactat cagctggtgc aacccatcat    2520
gctctccgat cagagcagag ccaagacaat actcctgcac ctgtggatca tgtccagcta    2580
cctgtcgact ttgtgcaggc gatgatgtct atgatggagg cgatatcaca gagggtaagt    2640
aaagttgact atcagctgga ccttgtcttg aaacagacat cttctatccc catgatgcgg    2700
tctgaaatcc agcagctgaa aacgtctgtt gcggtcatgg aagccaattt gggcatgatg    2760
aagatcctgg accctggttg tgccaacgtt tcatctctaa gtgatctacg ggcagttgcc    2820
cgatcccacc cggttttaat ttctggcccc ggagacccat ctccttatgt gacccaaggg    2880
ggcgaaatgg cactcaataa actttcgcaa ccggtgcaac cccctctga attgattaaa    2940
cccgccacgg caagcgggcc tgatataggg gtggagaaag acactgtccg tgcattgatc    3000
atgtcacgcc ctatgcatcc gagctcttca gctaggctct tgagcaaact ggacgcagcc    3060
ggatcgattg aggaaatcag aaaaatcaag cgccttgcac tgaatggcta atcaccaccg    3120
caacccgcag cagatccctg tccacccagc accacggt atctgcacca agctcctctc    3180
tgcaaaccca aggtccaaca ccccgagcga caaccctgtc ctgcttcctc tgccccacta    3240
aatgatcgcg cagctgcaat caattcagct atattaagga ttaagaaaaa atacgggtag    3300
aatcggagtg ccccgattgt gccaagatgg actcatctag acaatcggg ctgtactttg    3360
attctacccct tccttctagc aacctgctag cattcccgat agtcctacaa gacacagggg    3420
acgggaagaa gcaaatcgcc ccgcaataca ggatccagcg tcttgactcg tggacagaca    3480
gcaaagaaga ctcggtattc atcaccacct atggattcat ctttcaggtt gggaatgaag    3540
aagccactgt cggcatgatc aatgataatc ccaagcgcga gttactttcc actgccatgc    3600
tatgcctagg gagtgtacca aatgtcggag atcttgttga gctggcaagg gcctgcctca    3660
ctatggtggt aacatgcaag aagagtgcaa ctaacaccga gagaatggtc ttctcagtag    3720
tgcaggcacc ccaggtgctg caaagctgta gggttgtggc aaacaaatac tcgtcggtga    3780
atgcagtcaa gcacgtgaaa gcaccagaga agattcctgg gagcggaacc ctagagtaca    3840
aagtgaactt tgtctctctg accgtggtgc caagaaagga cgtctacaag ataccaactg    3900
cagcacttaa ggtctctggc tcaagtctgt acaatcttgc gctcaatgtc actattgatg    3960
tggaggtaga cccgaagagc ccgttggtca atccctttc caagtccgac agtgggtact    4020
atgctaatct cttcttacat attgggctta tgtccactgt agataagaag gggaagaaag    4080
tgacatttga caagctggaa aggaagataa ggagacttga tctatctgta gggcttagtg    4140
acgtgctcgg accttccgtg cttgtaaagg cgagaggtgc acggactaag ctgctggcac    4200
ctttcttctc tagcagtggg acagcctgct atcccatagc aaatgcctct cctcaggtgg    4260
ccaagatact ctggagccaa accgcgtacc tgcggagtgt aaaagtcatt atccaagcgg    4320
gcacccagcg tgctgtcgca gtgaccgccg accacgaggt tacctctact aagctggaga    4380
aggggcatac cattgccaaa tacaatccct tcaagaaata ggctgcatct ctgagattgc    4440
actccgccca tcttcccgga tcaccatgac actaaataat gatctgtctt gattacttat    4500
agttagttcg cctgtctatc aaattagaaa aaacacgggt agaagattct ggatcccggt    4560
tggcgccttc aaggtgcaag atgggctcca gatcttctac caggatccca gtacctctta    4620
tgctgaccgt ccgagtcatg ttggcactga gttgcgtctg tccgaccagc gcccttgatg    4680
gcaggcctct tgcagctgca gggattgtgg taacaggaga caaagcagtc aacatataca    4740
```

```
cctcatctca gacagggtca atcataatca agttactccc aaatatgccc aaggataaag   4800
aggcgtgtgc aaaagccccg ttggaggcat acaacaggac attgactact ttgctcaccc   4860
cccttggtga ttctatccgt aggatacaag agtctgtgac cacgtccgga ggagggaaac   4920
agggacgtct tataggcgcc attatcggtg gtgtagctct cggggttgca accgctgcac   4980
agataacagc agcctcggct ctgatacaag ccaatcaaaa tgctgccaac atactccggc   5040
taaaagagag cattgctgca accaatgagg ctgtgcacga ggtcactaat ggattatcac   5100
aactagcagt ggcagttggg aagatgcagc aatttgttaa tgaccagttt aataaaacag   5160
ctcaggaatt ggactgtata aaaattacac agcaggttgg tgtagaactc aacctgtacc   5220
taactgaatt gactacagta ttcgggccac aaatcacttc ccctgcctta actcagctga   5280
ctatccaggc gctttacaat ctagctggtg ggaatatgga ttacttgttg actaagttag   5340
gtgtggggaa caaccaactc agctcattaa ttagtagtgg cctgatcacc ggcaacccta   5400
ttctgtacga ctcacagact caactcttgg gtatacaggt aaccctaccc tcagtcggga   5460
acctaaataa tatgcgtgcc acctacctgg aaaccttgtc tgtaagtaca accaaaggat   5520
ttgcctcagc acttgtccca aaagtagtga cacaggtcgg ttccgtgata gaagagcttg   5580
acacctcgta ctgtatagag accgatttgg atctatattg tacaagaata gtgacattcc   5640
ctatgtctcc tggtatttat tcctgtttga gtggcaatac atctgcttgc atgtactcaa   5700
agactgaagg cgcactcact acgccgtata tgaccctcaa aggctcagtt attgctaact   5760
gtaagatgac aacatgtaga tgtgcagacc ccccgggtat catatcgcaa aattatggag   5820
aagctgtgtc tctaatagat aggcaatcat gcaatatctt atccttagac gggataactt   5880
tgaggctcag tggggaattt gatgcaactt atcaaaagaa tatctcaata caagattctc   5940
aagtaatagt gacaggcaat cttgatatct cgactgagct tgggaatgtc aacaactcga   6000
taagtaatgc tttggataag ttagaggaaa gcaacagcaa actagataag gtcaatgtca   6060
aactgaccag cacatccgct cttattacct atatcgtttt aactgtcata tctcttgtat   6120
gtggtatact tagcctggtt ctagcatgct acctgatgta caagcaaaag gcgcaacaga   6180
agaccttgtt gtggcttggg aataataccc tagaccagat gagggccact acaaaaatgt   6240
gaatgcggat gagaggcaga acatccccca atagcagttt gtgtgtaaag tctgacagcc   6300
tgttaattag aagaattaag aaaaaactac cggatgtaga tgaccaaagg gcgatatacg   6360
ggtagaacgg tcggggaggc cgtccctcaa tcgggagccg ggcctcacaa catccgttct   6420
accgcatcac caatagcagt tttcagtcat ggaccgcgca gttagccaag ttgcgctaga   6480
gaatgatgaa agagaggcaa agaatacatg gcgcttggta ttccggatcg caatcctact   6540
ctcaacggtg gtgaccttag ccatctctgc agccgccctt gcatatagca tggaggccag   6600
cacacctagc gatcttgtag gcataccgac tgcgatctct agagcagagg aaaagattac   6660
atctgcactc ggttccaatc aagatgtagt agataggata tataagcagg tggccctcga   6720
atctccactg gcattgctaa acaccgaatc tacaattatg aacgcaataa cgtctctctc   6780
ttatcgaatc aatggggccg caaatagcag cggatgtgga gcacccattc atgatccaga   6840
ttatattgga ggaataggta aagaacttat tgtgagtgat gctagcgacg tcacatcata   6900
ctatccctct gcgttccaag aacacctgaa ctttatcccg gcgcctacta caggatcagg   6960
ttgcactcgg ataccctcat ttgacatgag cgctacccac tactgttata ctcacaatgt   7020
gatattatct ggctgcagag atcactcgca ctcacatcaa tatttagcac ttggtgtgct   7080
```

```
tcggacatct gcaacaggga gggtattctt ttccactctg cgttccatca atctggatga      7140
cacccaaaat cggaagtctt gcagtgtgag tgcaaccccc ttgggttgtg atatgctgtg      7200
ctctaaagtc acagagactg aagaagagga ttataactca gctatcccca cgtcgatggt      7260
acatggaagg ttagggttcg acggccaata ccacgagaag gacctagatg tcacaacact      7320
attcgaggac tgggtggcaa actacccagg agtagggggc gggtctttta ttgacaaccg      7380
cgtatggttc ccagtttacg gagggctaaa acccaattcg cccagtgaca ccgcacaaga      7440
agggaaatat gtaatataca agcgatacaa tgacacatgt ccagatgagc aagattatca      7500
gattcaaatg gctaagtctt catataagcc tgggcggttt ggagggaaac gcgtacagca      7560
ggccatctta tctatcaaag tgtcaacatc cttgggcgag acccggtac tgactgtacc       7620
gcccaacaca gtaacactca tggggccga aggcagagtt ctcacagtag gacatctca       7680
tttcctttat cagcgagggt catcatactt ctcccctgcc ctactatatc ctatgatagt      7740
cagcaacaaa acagccactc ttcatagtcc ttatacattc aatgccttca ctcgaccagg      7800
tagtgtccct tgccaggctt cagcaagatg ccctaactca tgtgttaccg gagtctatac      7860
tgatccatat cccttggtct tctataggaa ccacaccttg cgaggggtat tcgggacgat      7920
gcttgatgat aaacaagcaa gactcaaccc tgtatctgca gtatttgaca gcatatcccg      7980
cagtcgcata acccgggtga gttcaagcag caccaaggca gcatacacaa catcaacatg      8040
ttttaaagtt gtaaagacca ataaaaccta ttgtctcagc attgccgaaa tatccaatac      8100
cctcttcggg gaattcagaa tcgtcccttt actagttgag attctcaagg atgatggggt      8160
tagagaagcc aggtctagcc ggttgagtca actgcgagag ggttggaaag atgacattgt      8220
atcacctatc ttttgcgacg ccaagaatca aactgaatac cggcgcgagc tcgagtccta      8280
cgctgccagt tggccataat cagctagtgc taatgtgatt agattaagtc ttgtcggtag      8340
tcacttgatt aagaaaaaat gtgggtggta gcgggatata aggcaaaaca actcaaggag      8400
gatagcacgg gtaggacatg gcgagctccg gtcccgagag ggcggagcat cagattatcc      8460
taccagagtc acacctgtct tcaccattag tcaagcacaa actactctat tactggaaat      8520
taactgggct accactccct gacgagtgtg acttcgacca cctcattctc agccgacaat      8580
ggaagaaaat acttgaatcg gcctcccctg acactgagag aatgataaaa cttggaaggg      8640
cagtgcacca gactctcaac cacaattcca agataaccgg agtactccat cccaggtgtt      8700
tagaagaatt ggctagtatt gaggttcctg actcaaccaa caagtttcgg aagatcgaga      8760
agaaaatcca aattcacaac acaaggtatg gagaactgtt cacaagactg tgcacgcatg      8820
tagagaagaa attgttggga tcatcttggt ctaataatgt cccccggtca gaagagttca      8880
acagcatccg tacagatccg gcattctggt ttcactcaaa atggtccaca actaagtttg      8940
catggctcca tataaaacag attcaaaggc atctgattgt ggcagcaaga acaaggtccg      9000
cagccaacaa attggtgacg ctgacccata aggtaggcca agtctttgtt actcctgagc      9060
ttgtcattgt gacacataca gatgagaaca agttcacgtg tcttacccag gaacttgtgt      9120
tgatgtatgc agatatgatg gagggcagag atatggtcaa cataatatca tccacggcgg      9180
cacatctcag gagcctatca gagaaaattg atgacattct gcggttagta gatgccctgg      9240
caaaagatct gggtaatcaa gtctacgatg ttgtagcact catggaggga tttgcatacg      9300
gcgccgtcca gctgcttgag ccgtcaggta cattcgcagg ggattcttc gcattcaacc       9360
tgcaggagct caaagacact ttgatcggcc tccttcctaa ggatatagca gaatctgtga      9420
ctcacgcaat agccactgta ttctctggct tagaacaaaa tcaagcggct gagatgctgt      9480
```

```
gcctgttgcg tctatggggc cacccattac ttgagtcccg tattgcggca aaagcagtaa     9540
ggagccaaat gtgcgcacca aaatggtag actttgatat gatcctccag gtattgtctt      9600
tctttaaagg aacaatcatc aacggataca gaaagaagaa tgcaggtgtt tggccacgtg     9660
tcaaagtaga tacgatatac gggaaggtca ttgggcagct acacgctgat tcagcggaga     9720
tttcacacga tatcatgttg agagagtaca agagtttatc tgcgcttgaa ttcgagccat     9780
gtatagaata cgaccctatc accaatctga gcatgtttct aaaagacaag gcgatcgcac     9840 accccgaaaga caactggctc gccgcgttta ggcgaaacct tctctctgag gaccagaaga    9900
aacatgtaaa ggaggcaacc tctactaacc gtctcttgat agagttctta gagtcaaatg     9960
attttgatcc atataaggag atggaatatc tgacgaccct tgagtaccta agagatgaca    10020
atgtggcagt atcatactcg ctcaaggaga aggaagtgaa ggttaatggg cggattttg     10080 ctaagctaac aaagaaatta aggaactgtc aagtgatggc ggaagggatc ttagctgacc    10140
agattgcacc tttctttcaa gggaatgggg tcattcagga tagcatatct ttaaccaaga    10200
gtatgctagc gatgagtcaa ttgtctttca acagcaataa gaaacgtatc actgactgca    10260
aagaaagagt agcctcaaac cgcaatcacg atcaaaagag caagaatcgt cggagagttg    10320
ccacttttat aacgactgac ctgcaaaagt actgtcttaa ttggagatat cagacaatca    10380
aactgttcgc tcatgccatc aatcagctga tgggcttacc tcacttcttc gaatggattc    10440
atctaagact aatggatact acgatgtttg taggagaccc tttcaatccc ccaagtgacc    10500
caactgactg tgatctctca agagtcccaa atgatgacat atatattgtc agtgctagag    10560
ggggtattga gggattatgt cagaagctat ggacaatgat ctcaattgct gcaatccaac    10620
ttgctgcagc aagatcacat tgtcgcgtcg cctgtatggt acagggtgac aatcaagtaa    10680
tagctgtaac gagagaggta aggtcagatg actccccgga aatggtgtta acacaattgc    10740
atcaagccag tgataatttc ttcaaggaat tgattcatgt taatcatttg attggccata    10800
atttgaagga tcgtgaaaca atcagatcag acacattctt catatacagc aaacgaatat    10860
tcaaagatgg agcaatactc agtcaagtcc tcaaaaattc atctaaatta gtgctaaatat   10920 caggcgacct tagtgaaaac accgtaatgt cctgtgccaa cattgcatct actatagcac    10980
ggctgtgcga gaacgggctt ccaaaggatt tctgttatta cttaaactac ctgatgagtt    11040
gcgtgcagac atactttgat tctgagtttt ccatcactaa cagctcgcac cccgattcta    11100
accagtcgtg gattgaagac atctcttttg tgcactcata tgtcctgacc cctgcccagc    11160 taggggact gagcaacctc caatactcaa ggctctacac gaggaacatc ggtgacccgg     11220
gaactactgc ttttgcagag atcaagcgat tagaagcagt ggggttacta agtcctagta    11280
ttatgactaa catcttaact aggccgcctg gaaatggaga ttgggccagt ctgtgtaacg    11340
acccttactc tttcaatttt gagactgtcg cgagtccaaa tattgtcctt aagaaacata    11400
cacaaagagt cctatttgaa acttgttcaa atcccttatt atctggcgtg catacagagg    11460
ataatgaggc agaagagaag gcgttggctg aattttact caatcaagaa gtaattcatc     11520
cacgtgtcgc acatgctatc atggaagcaa gctctatagg taggaggaag cagattcaag    11580
ggcttgttga cacaacaaac accgtaatca agattgcatt gactaggagg ccacttggca    11640
tcaagaggct gatgcggata gttaactact cgagcatgca tgcaatgctg tttagagacg    11700
atgttttctc atctaacagg tctaaccacc ccttagtttc ctctaatatg tgttctctga    11760
cgctagcaga ctatgcacgg aatagaagct ggtcaccatt gacgggggt agaaagatac     11820
```

```
tgggtgtatc taatcctgat actatagaac ttgtagaggg tgagatcctt agcgtcagcg    11880
gaggatgcac aagatgtgac agcggagatg aacaattcac ttggttccat cttccgagca    11940
atatagaact gaccgatgac accagcaaga atcctccgat gagagtgccg tacctcgggt    12000
caaagactca agagaggagg gccgcctcgc ttgcgaaaat agctcatatg tcaccacatg    12060
tgaaagctgc tctaagggca tcatccgtgt tgatctgggc ttatggagac aacgaagtaa    12120
attggactgc tgctcttaaa attgcaagat ctcggtgcaa tataaactca gagtatcttc    12180
gactattgtc ccccttaccc acagctggga atctccaaca tagactggat gacggcataa    12240
ctcagatgac attcacccct gcatctctct acagggtgtc accttatatt cacatatcca    12300
atgattctca aaggttattc acggaagaag gagtcaaaga gggaaatgta gtttatcagc    12360
aaatcatgct cttgggttta tctctaatcg aatcactctt cccgatgacg acaaccagga    12420
catacgatga gatcacattg cacctccaca gtaaatttag ctgctgtatc agggaagcac    12480
cggttgcagt tcctttcgag ttactcggga tggcaccaga actaaggaca gtgacctcaa    12540
ataagtttat gtatgatcct agtcctgtat cggagggtga ctttgcgaga cttgacttag    12600
ctatctttaa gagttatgag cttaatctag aatcatatcc cacaatagag ctaatgaaca    12660
ttctttcaat atccagcggg aagttaatcg gccagtctgt ggtttcttat gatgaagata    12720
cctccataaa gaatgacgcc ataatagtgt atgacaacac ccggaattgg atcagcgaag    12780
ctcagaattc agatgtggtc cgcctattcg agtatgcagc acttgaagtg cttctcgact    12840
gttcttatca gctctactat ctgagagtaa gaggcctaga caatatcgtg ttgtatatga    12900
gtgacttata taagaatatg ccaggaattc tactttccaa cattgcagct acaatatctc    12960
atcccatcat tcattcaaga ttgcatgcag taggcctggt caatcacgac gggtcacacc    13020
aacttgcaga cacagatttc atcgaaatgt ctgcaaaact attagtctct tgcactcgac    13080
gcgtggtctc aggtttatat gcagggaata gtatgatct gctgttcccg tctgtcttag    13140
atgataacct gagtgagaag atgcttcagc tgatatctcg gttatgctgc ctgtatacgg    13200
tgctctttgc tacaacaaga gagatcccga aaataagagg cttatctgca gaagagaagt    13260
gttcagtact tactgagtac ctactgtcag atgctgtgaa accattactt agttctgagc    13320
aagtgagctc tatcatgtct cctaacatag ttacgttccc agctaatcta tattacatgt    13380
ctcggaagag ccttaatttg attagggaaa gagaggacag ggacactatc ttggcattgt    13440 tgttcccccca agagccacta cttgagttcc ccttagtaca agatattggc gctcgagtga    13500
aagatccatt cacccgacaa cctgcggcgt ttttacaaga attagatttg agcgctccag    13560
caaggtatga cgcatttaca cttagtcagg ttcattctga acacacatca ccaaatccgg    13620
aggacgacta cttagtacga tacctgttca gaggaatagg gaccgcgtcc tcctcttggt    13680
ataaggcatc tcaccttctt tctgtacctg aggtcagatg tgcaaggcac gggaattcct    13740
tatacttggc agaaggaagc ggagccatta tgagtcttct cgaactgcat gtgccgcatg    13800
agactatcta ttacaatacg ctcttctcaa acgagatgaa ccccccacag cggcatttcg    13860
gaccgacccc aacacagttt ctgaattcag ttgttatag aatctacag gcggaggtac    13920 catgtaagga tggatttgtc caggagttcc gtccattatg gagagagaat acagaagaaa    13980
gcgatctgac ctcagataaa gcagtggggtt acatcacatc tgcagtgccc taccggtctg    14040
tatcattgct gcactgtgac attgagattc ctccaggatc caatcaaagc ttactggatc    14100
aactggctac caatctgtct ctgattgcca tgcattctgt aagggagggc ggggtcgtga    14160
tcatcaaagt gttgtatgca atgggatatt acttccatct actcatgaac ttgttcactc    14220
```

```
cgtgttctac gaaaggatat attctctcta atggctatgc atgtagaggg gatatggagt   14280
gttacctggt atttgtcatg ggctatcgag gtgggcctac atttgtacat gaggtagtga   14340
ggatggcaaa aactctagtg cagcggcacg gtacactttt gtccaaatca gatgagatca   14400
cactgactag gttatttacc tcacagcggc agcgtgtaac agacatccta tccagtcctt   14460
taccgagact aataaagttc ttgagaaaga atatcgatac tgcgctaatt gaagccgggg   14520
gacaacccgt ccgtccattc tgtgcagaga gcttggtgag gacactagcg gacacaactc   14580
agatgaccca gatcatcgct agtcacattg acacagtcat tcgatctgtg atctacatgg   14640
aggctgaggg tgatctcgcc gacacagtgt tcttatttac cccctacaat ctctctacag   14700
acggtaaaaa gagaacatca cttaaacagt gcacaaggca gatcttagag gtcacaatat   14760
tgggtcttag agttgaaaat ctcaataaag taggtgatgt agtcagtcta gtacttaaag   14820
gtatgatttc tctggaggac ctgatccctc taagaacata cttgaagcgt agtacctgcc   14880
ctaagtattt gaagtctgtt ctaggtatta ctaaactcaa agaaatgttt acagacacct   14940
ctttattata cttgactcgt gctcaacaaa aattctacat gaaaactata ggcaacgcag   15000
tcaagggata ctacagtaac tgtgactctt aaagataatc acatattaat aggctccttt   15060
tctagttaac tgagcccttg ttgatttaat gatactatat tagaaaaaag ttgcactccg   15120
atcctttagg actcgtgttc gaattcaaat aattgtctta gaaaaaagtt gcgcgtaatt   15180
gttcttgaat gtagtcctgt cattcaccaa atctttgttt ggtcggcatg gcatctccac   15240
ctcctcgcgg tccgacctgg gcatccgaag gaggacgcac gtccactcgg atggctaagg   15300
gagtagcata accccttggg gcctctaaac gggtcttgag gggtttttg ggcgcgccgt   15360 cgaccgatgc ccttgagagc cttcaaccca gtcagctcct tccggtgggc gcggggcatg   15420
actatcgtcg ccgcacttat gactgtcttc tttatcatgc aactcgtagg acaggtgccg   15480
gcagcgctct gggtcatttt cggcgaggac cgctttcgct ggagcgcgac gatgatcggc   15540
ctgtcgcttg cggtattcgg aatcttgcac gccctcgctc aagccttcgt cactggtccc   15600
gccaccaaac gtttcggcga gaagcaggcc attatcgccg gcatggcggc cgacgcgctg   15660
ggctacgtct tgctggcgtt cgcgacgcga ggctggatgg ccttccccat tatgattctt   15720
ctcgcttccg gcggcatcgg gatgcccgcg ttgcaggcca tgctgtccag gcaggtagat   15780
gacgaccatc agggacagct tcaaggatcg ctcgcggctc ttaccagcct aacttcgatc   15840
actggaccgc tgatcgtcac ggcgatttat gccgcctcgg cgagcacatg aacgggttg   15900 gcatggattg taggcgccgc cctataccctt gtctgcctcc ccgcgttgcg tcgcggtgca   15960
tggagccggg ccacctcgac ctgaatggaa gccggcggca cctcgctaac ggattcacca   16020
ctccaagaat tggagccaat caattcttgc ggagaactgt gaatgcgcaa accaaccctt   16080
ggcagaacat atccatcgcg tccgccatct ccagcagccg cacgcggcgc atctcgggca   16140
gcgttgggtc ctggccacgg gtgcgcatga tcgtgctcct gtcgttgagg acccggctag   16200
gctggcgggg ttgccttact ggttagcaga atgaatcacc gatacgcgag cgaacgtgaa   16260
gcgactgctg ctgcaaaacg tctgcgacct gagcaacaac atgaatggtc ttcggtttcc   16320
gtgtttcgta aagtctggaa acgcggaagt cagcgccctg caccattatg ttccggatct   16380
gcatcgcagg atgctgctgg ctaccctgtg gaacacctac atctgtatta acgaagcgct   16440
ggcattgacc ctgagtgatt tttctctggt cccgccgcat ccataccgcc agttgtttac   16500
cctcacaacg ttccagtaac cgggcatgtt catcatcagt aacccgtatc gtgagcatcc   16560
```

-continued

```
tctctcgttt catcggtatc attacccca tgaacagaaa tcccccttac acggaggcat    16620
cagtgaccaa acaggaaaaa accgcccttt acatggcccg ctttatcaga agccagacat   16680
taacgcttct ggagaaactc aacgagctgg acgcggatga acaggcagac atctgtgaat   16740
cgcttcacga ccacgctgat gagctttacc gcagctgcct cgcgcgtttc ggtgatgacg   16800
gtgaaaacct ctgacacatg cagctcccgg agacggtcac agcttgtctg taagcggatg   16860
ccgggagcag acaagcccgt cagggcgcgt cagcgggtgt tggcgggtgt cggggcgcag   16920
ccatgaccca gtcacgtagc gatagcggag tgtatactgg cttaactatg cggcatcaga   16980
gcagattgta ctgagagtgc accatatgcg gtgtgaaata ccgcacagat gcgtaaggag   17040
aaaataccgc atcaggcgct cttccgcttc ctcgctcact gactcgctgc gctcggtcgt   17100
tcggctgcgg cgagcggtat cagctcactc aaaggcggta atacggttat ccacagaatc   17160
aggggataac gcaggaaaga acatgtgagc aaaaggccag caaaaggcca ggaaccgtaa   17220
aaaggccgcg ttgctggcgt ttttccatag gctccgcccc cctgacgagc atcacaaaaa   17280
tcgacgctca agtcagaggt ggcgaaaccc gacaggacta taaagatacc aggcgtttcc   17340
ccctggaagc tccctcgtgc gctctcctgt tccgaccctg ccgcttaccg gatacctgtc   17400
cgcctttctc ccttcgggaa gcgtggcgct ttctcatagc tcacgctgta ggtatctcag   17460
ttcggtgtag gtcgttcgct ccaagctggg ctgtgtgcac gaaccccccg ttcagcccga   17520
ccgctgcgcc ttatccggta actatcgtct tgagtccaac ccggtaagac acgacttatc   17580
gccactggca gcagccactg gtaacaggat tagcagagcg aggtatgtag gcggtgctac   17640
agagttcttg aagtggtggc ctaactacgg ctacactaga aggacagtat ttggtatctg   17700
cgctctgctg aagccagtta ccttcggaaa aagagttggt agctcttgat ccggcaaaca   17760
aaccaccgct ggtagcggtg ttttttttgt ttgcaagcag cagattacgc gcagaaaaaa   17820
aggatctcaa gaagatcctt tgatcttttc tacgggtct gacgctcagt ggaacgaaaa   17880
ctcacgttaa gggattttgg tcatgagatt atcaaaagg atcttcacct agatcctttt   17940
aaattaaaaa tgaagtttta aatcaatcta agtatatat gagtaaactt ggtctgacag   18000
ttaccaatgc ttaatcagtg aggcacctat ctcagcgatc tgtctatttc gttcatccat   18060
agttgcctga ctccccgtcg tgtagataac tacgatacgg gagggcttac catctggccc   18120
cagtgctgca atgataccgc gagacccacg ctcaccggct ccagatttat cagcaataaa   18180
ccagccagcc ggaagggccg agcgcagaag tggtcctgca actttatccg cctccatcca   18240
gtctattaat tgttgccggg aagctagagt aagtagttcg ccagttaata gtttgcgcaa   18300
cgttgttgcc attgctgcag gcatcgtggt gtcacgctcg tcgtttggta tggcttcatt   18360
cagctccggt tcccaacgat caaggcgagt tacatgatcc cccatgttgt gcaaaaaagc   18420
ggttagctcc ttcggtcctc cgatcgttgt cagaagtaag ttggccgcag tgttatcact   18480
catggttatg gcagcactgc ataattctct tactgtcatg ccatccgtaa gatgcttttc   18540
tgtgactggt gagtactcaa ccaagtcatt ctgagaatag tgtatgcggc gaccgagttg   18600
ctcttgcccg gcgtcaacac gggataatac cgcgccacat agcagaactt taaaagtgct   18660
catcattgga aaacgttctt cggggcgaaa actctcaagg atcttaccgc tgttgagatc   18720
cagttcgatg taacccactc gtgcacccaa ctgatcttca gcatctttta ctttcaccag   18780
cgtttctggg tgagcaaaaa caggaaggca aaatgccgca aaaaagggaa taagggcgac   18840
acggaaatgt tgaatactca tactcttcct ttttcaatat tattgaagca tttatcaggg   18900
ttattgtctc atgagcggat acatatttga atgtatttag aaaaataaac aaatagggt    18960
```

| | |
|---|---|
| tccgcgcaca tttccccgaa aagtgccacc tgacgtctaa gaaaccatta ttatcatgac | 19020 |
| attaacctat aaaaataggc gtatcacgag gcccttctgt cttcaagaat tctaatacga | 19080 |
| ctcactatag g | 19091 |

<210> SEQ ID NO 2
<211> LENGTH: 20278
<212> TYPE: DNA
<213> ORGANISM: Artificial Sequence
<220> FEATURE:
<223> OTHER INFORMATION: LVP-K1-RBD19

<400> SEQUENCE: 2

| | |
|---|---|
| accaaacaga gaatccgtaa ggtacgatag aaggcgaagg agcaatcgaa gtcgtacggg | 60 |
| tagaaggtgt gaatctcgag tgcgagcccg aagctcaaac tcgagagagc cttctgccaa | 120 |
| aatgtcttct gtattcgatg agtacgagca gctcctcgcg gctcagactc gccccaatgg | 180 |
| agctcatggc ggaggagaga aggggagcac cttaaaggta gaagtcccgg tattcactct | 240 |
| caacagtgat gacccagaag atagatggaa cttttgcagtg ttttgtcttc ggattgctgt | 300 |
| tagcgaggat gccaacaaac cacttaggca aggtgctctc atatctctct tatgttccca | 360 |
| ctctcaagtg atgaggaacc atgttgccct tgcggggaaa cagaatgagg ccacactggc | 420 |
| tgttcttgag atcgatggtt ttaccaacgg cgtgccccag ttcaacaaca ggagtggagt | 480 |
| gtctgaagag agagcacaga gatttatgat gatagcaggg tctctccctc gggcatgcag | 540 |
| caacggtacc ccgttcgtca cagctggggt tgaagatgat gcaccagaag acattactga | 600 |
| taccctggag aggatcctct ctatccaggc tcaagtatgg gtcacggtgg caaaggccat | 660 |
| gactgcatat gagacagcag atgagtcaga aacaagaaga atcaataagt acatgcagca | 720 |
| aggcagggtc cagaagaagt acatcctcca ccccgtatgc aggagcgcaa tccaactcac | 780 |
| aatcagacag tctctggcgg tccgcatctt tttggttagc gagcttaaga gaggccgcaa | 840 |
| cacggcaggt gggacctcca cctattacaa cttggtgggg gatgtagact catacatcag | 900 |
| gaacactggg ctaactgcat tcttcctgac acttaaatat ggaattaaca ccaagacatc | 960 |
| agcccttgca cttagcagcc tctcaggcga tatccagaaa atgaagcagc tcatgcgctt | 1020 |
| gtatcgatg aaaggagata atgcgccgta catgacattg ctcggtgaca gtgaccagat | 1080 |
| gagctttgca cctgccgagt atgcacaact ttactccttt gccatgggta tggcatcagt | 1140 |
| cctagataaa ggaactagca ataccaatt tgccagggac tttatgagca catcattctg | 1200 |
| gagacttgga gtagagtacg ctcaggctca aggaagtagc atcaatgagg atatggccgc | 1260 |
| cgagctaaag ctaaccccag cagcaaggag aggcctggca gctgctgccc aaagagtgtc | 1320 |
| tgaggagacc agcagcatgg acatgcccac ccaacaagcc gggtcctca ctggactcag | 1380 |
| cgacggaggc tcccaagccc ccaaggtgc actgaacaga tcacaagggc aaccggacac | 1440 |
| cggggatggg gagacccaat ttctggatct gatgagagcg tggcaaata gcatgagaga | 1500 |
| agcgccaaac tctgcgcagg gcaccctca accggggcct ccccaaccc ctgggccctc | 1560 |
| tcaagacaat gacaccgact gggggtactg accgacagca cccagtttgc ttctatgagg | 1620 |
| tcatcccaat tcctctgctt agaaaaaata cgggtagaag cggccgcggc cggccaccat | 1680 |
| gggctccaga tcttctacca ggatcccagt acctcttatg ctgaccgtcc gagtcatgtt | 1740 |
| ggcactgagt tgcgtctgtc cgaccagcgc ccttgatggc aggcctcttg cagctgcagg | 1800 |
| gattgtggta acaggagaca aagcagtcaa catatacacc tcatctcgaa cagggtcaat | 1860 |

```
cataatcaag ttactcccaa atatgcccaa ggataaagag gcgtgtgcaa aagcccgtt      1920 ggaggcatac aacaggacat tgactacttt gctcaccccc cttggtgatt ctatccgtag      1980
gatacaagag tctgtgacca cgtccggagg agggaaacag ggacgtctta taggcgccat      2040
tatcggtggt gtagctctcg ggttgcaac cgctcaccac catcaccacc atcacaatat      2100
tacaaacttg tgccctttg gtgaagtttt taacgccacc agatttgcat ctgtttatgc      2160
ttggaacagg aagagaatca gcaactgtgt tgctgattat tctgtcctat ataattccgc      2220 atcatttcc acttttaagt gttatggagt gtctcctact aaattaaatg atctctgctt      2280
tactaatgtc tatgcagatt catttgtaat tagaggtgat gaagtcagac aaatcgctcc      2340
agggcaaact ggaaagattg ctgattataa ttataaatta ccagatgatt ttacaggctg      2400
cgttatagct tggaattcta acaatcttga ttctaaggtt ggtggtaatt ataattccct      2460
gtatagattg tttaggaagt ctaatctcaa accttttgag agagatattt caactgaaat      2520
ctatcaggcc ggtagcacac cttgtaatgg tgttgaaggt tttaattgtt actttccttt      2580
acaatcatat ggtttccaac ccactaatgg tgttggttac caaccataca gagtagtagt      2640 actttcttt gaacttctac atgcaccagc aactgtttgt ggaccttccg ctcttattac      2700
ctatatcgtt ttaactgtca tatctcttgt atgtggtata cttagcctgg ttctagcatg      2760
ctacctgatg tacaagcaaa aggcgcaaca aagaccttg ttgtggcttg gaataatac       2820 cctagaccag atgaggggcca ctacaaaaat gtgaggccgg ccccacaccc cacccctcaa      2880
tccgcaatcc cgcatggcca aacccacaaa cgaaccccc tgtctccctc ctctccccca      2940
gccccacaac cccacctgcc cagggcaaca taggtacaat gcgacccact aataatcaat      3000
acagggccaa agaaattaga aaaaagtacg ggtagaaggg agacattcag agatcagggc      3060
gagtcacccg ggtctctgct ctcccttcta cctagtggat taggatggag atggccacct      3120
ttacagatgc ggagatcgac gagctatttg agaccagtgg aactgtcatt gacagcataa      3180
ttacggccca gggaaaacca gtagagactg ttggaaggag tgcaatccca caaggcaaaa      3240
ctaaggcttt gagcgcagca tgggagaagc atgggagcat ccagtcacca gccagccaag      3300 acaccctga tcgacaggac agatcagata aacaactgtc cacacccgag caagcgagtc      3360
caaacgacag ccccccagcc acatccactg accagcctcc cactcaggct gcagatgagg      3420
ccggcgatac acagctcaag accggagcaa gcaactctct gctgtcgatg cttgataaac      3480
tcagcaataa gtcatctaat gctaaaaagg gcccagggtc gagccctcaa gaaaggcatc      3540
atcaacgtct gactcaacaa caggggagtc aacaaagccg cggaaacagc caagagagac      3600
cgcagaacca ggccaaggcc atccctggaa accaggtcac agacgcgaac acagcatatc      3660
atggacaatg ggaggagtca caactatcag ctggtgcaac ccatcatgct ctccgatcag      3720
agcagagcca agacaatact cctgcacctg tggatcatgt ccagctacct gtcgactttg      3780
tgcaggcgat gatgtctatg atggaggcga tatcacagag ggtaagtaaa gttgactatc      3840
agctggacct tgtcttgaaa cagacatctt ctatccccat gatgcggtct gaaatccagc      3900
agctgaaaac gtctgttgcg gtcatggaag ccaatttggg catgatgaag atcctggacc      3960
ctggttgtgc caacgtttca tctctaagtg atctacgggc agttgcccga tcccacccgg      4020 ttttaattc tggccccgga gacccatctc cttatgtgac ccaaggggc gaaatggcac       4080 tcaataaact ttcgcaaccg gtgcaacacc cctctgaatt gattaaaccc gccacggcaa      4140
gcgggcctga tataggagtg gagaaagaca ctgtccgtgc attgatcatg tcacgcccta      4200
tgcatccgag ctcttcagct aggctcttga gcaaactgga cgcagccgga tcgattgagg      4260
```

```
aaatcagaaa aatcaagcgc cttgcactga atggctaatc accaccgcaa cccgcagcag    4320
atccctgtcc acccagcacc acacggtatc tgcaccaagc tcctctctgc aaacccaagg    4380
tccaacaccc cgagcgacaa ccctgtcctg cttcctctgc cccactaaat gatcgcgcag    4440
ctgcaatcaa ttcagctata ttaaggatta agaaaaaata cgggtagaat cggagtgccc    4500
cgattgtgcc aagatggact catctaggac aatcgggctg tactttgatt ctacccttcc    4560
ttctagcaac ctgctagcat tcccgatagt cctacaagac acaggggacg ggaagaagca    4620
aatcgccccg caatacagga tccagcgtct tgactcgtgg acagacagca agaagactc     4680 ggtattcatc accacctatg gattcatctt tcaggttggg aatgaagaag ccactgtcgg    4740
catgatcaat gataatccca agcgcgagtt actttccact gccatgctat gcctagggag    4800
tgtaccaaat gtcggagatc ttgttgagct ggcaagggcc tgcctcacta tggtggtaac    4860
atgcaagaag agtgcaacta acaccgagag aatggtcttc tcagtagtgc aggcacccca    4920
ggtgctgcaa agctgtaggg ttgtggcaaa caaatactcg tcggtgaatg cagtcaagca    4980
cgtgaaagca ccagagaaga ttcctgggag cggaacccta gagtacaaag tgaactttgt    5040
ctctctgacc gtggtgccaa gaaggacgt ctacaagata ccaactgcag cacttaaggt     5100
ctctggctca agtctgtaca atcttgcgct caatgtcact attgatgtgg aggtagaccc    5160
gaagagcccg ttggtcaaat cccttttccaa gtccgacagt gggtactatg ctaatctctt   5220
cttacatatt gggcttatgt ccactgtaga taagaagggg aagaaagtga catttgacaa    5280
gctggaaagg aagataagga gacttgatct atctgtaggg cttagtgacg tgctcggacc    5340
ttccgtgctt gtaaaggcga gaggtgcacg gactaagctg ctggcacctt tcttctctag   5400
cagtgggaca gcctgctatc ccatagcaaa tgcctctcct caggtggcca agatactctg    5460
gagccaaacc gcgtacctgc ggagtgtaaa agtcattatc caagcgggca cccagcgtgc    5520
tgtcgcagtg accgccgacc acgaggttac ctctactaag ctggagaagg ggcataccat    5580
tgccaaatac aatcccttca agaaataggc tgcatctctg agattgcact ccgcccatct    5640
tcccggatca ccatgacact aaataatgat ctgtcttgat tacttatagt tagttcgcct    5700
gtctatcaaa ttagaaaaaa cacgggtaga agattctgga tcccggttgg cgccttcaag    5760
gtgcaagatg ggctccagat cttctaccag gatcccagta cctcttatgc tgaccgtccg    5820
agtcatgttg gcactgagtt gcgtctgtcc gaccagcgcc cttgatggca ggcctcttgc    5880
agctgcaggg attgtggtaa caggagacaa agcagtcaac atatacacct catctcagac    5940
agggtcaatc ataatcaagt tactcccaaa tatgcccaag gataaagagg cgtgtgcaaa    6000
agccccgttg gaggcataca acaggacatt gactactttg ctcaccccccc ttggtgattc   6060 tatccgtagg atacaagagt ctgtgaccac gtccggagga gggaaacagg gacgtcttat    6120
aggcgccatt atcggtggtg tagctctcgg ggttgcaacc gctgcacaga taacagcagc    6180
ctcggctctg atacaagcca atcaaaatgc tgccaacata ctccggctaa agagagcat    6240 tgctgcaacc aatgaggctg tgcacgaggt cactaatgga ttatcacaac tagcagtggc    6300
agttgggaag atgcagcaat tgttaatga ccagtttaat aaaacagctc aggaattgga    6360
ctgtataaaa attacacagc aggttggtgt agaactcaac ctgtacctaa ctgaattgac    6420
tacagtattc gggccacaaa tcacttcccc tgccttaact cagctgacta ccaggcgct    6480 ttacaatcta gctggtggga atatggatta cttgttgact aagttaggtg tggggaacaa    6540
ccaactcagc tcattaatta gtagtggcct gatcaccggc aaccctattc tgtacgactc    6600
```

-continued

```
acagactcaa ctcttgggta tacaggtaac cctaccctca gtcgggaacc taaataatat    6660
gcgtgccacc tacctggaaa ccttgtctgt aagtacaacc aaaggatttg cctcagcact    6720
tgtcccaaaa gtagtgacac aggtcggttc cgtgatagaa gagcttgaca cctcgtactg    6780
tatagagacc gatttggatc tatattgtac aagaatagtg acattcccta tgtctcctgg    6840
tatttattcc tgtttgagtg gcaatacatc tgcttgcatg tactcaaaga ctgaaggcgc    6900
actcactacg ccgtatatga ccctcaaagg ctcagttatt gctaactgta agatgacaac    6960
atgtagatgt gcagaccccc cgggtatcat atcgcaaaat tatggagaag ctgtgtctct    7020
aatagatagg caatcatgca atatcttatc cttagacggg ataactttga ggctcagtgg    7080
ggaatttgat gcaacttatc aaaagaatat ctcaatacaa gattctcaag taatagtgac    7140
aggcaatctt gatatctcga ctgagcttgg gaatgtcaac aactcgataa gtaatgcttt    7200
ggataagtta gaggaaagca acagcaaact agataaggtc aatgtcaaac tgaccagcac    7260
atccgctctt attacctata tcgttttaac tgtcatatct cttgtatgtg gtatacttag    7320
cctggttcta gcatgctacc tgatgtacaa gcaaaaggcg caacagaaga ccttgttgtg    7380
gcttgggaat aatacccctag accagatgag ggccactaca aaaatgtgaa tgcggatgag    7440
aggcagaaac atccccaata gcagtttgtg tgtaaagtct gacagcctgt taattagaag    7500
aattaagaaa aaactaccgg atgtagatga ccaaagggcg atatacgggt agaacggtcg    7560
gggaggccgt ccctcaatcg ggagccgggc ctcacaacat ccgttctacc gcatcaccaa    7620
tagcagtttt cagtcatgga ccgcgcagtt agccaagttg cgctagagaa tgatgaaaga    7680
gaggcaaaga atacatggcg cttggtattc cggatcgcaa tcctactctc aacggtggtg    7740
accttagcca tctctgcagc cgcccttgca tatagcatgg aggccagcac acctagcgat    7800
cttgtaggca taccgactgc gatctctaga gcagaggaaa agattacatc tgcactcggt    7860
tccaatcaag atgtagtaga taggatatat aagcaggtgg ccctcgaatc tccactggca    7920
ttgctaaaca ccgaatctac aattatgaac gcaataacgt ctctctctta tcgaatcaat    7980
ggggccgcaa atagcagcgg atgtggagca cccattcatg atccagatta tattggagga    8040
ataggtaaag aacttattgt agatgatgct agcgacgtca catcatacta tccctctgcg    8100
ttccaagaac acctgaactt tatcccggcg cctactacag gatcaggttg cactcggata    8160
ccctcatttg acatgagcgc tacccactac tgttatactc acaatgtgat attatctggc    8220
tgcagagatc actcgcactc acatcaatat ttagcacttg gtgtgcttcg gacatctgca    8280
acagggaggg tattcttttc cactctgcgt tccatcaatc tggatgacac ccaaaatcgg    8340
aagtcttgca gtgtgagtgc aaccccttg ggttgtgata tgctgtgctc taaagtcaca    8400
gagactgaag aagaggatta taactcagct atccccacgt cgatggtaca tggaaggtta    8460
gggttcgacg gccaatacca cgagaaggac ctagatgtca caacactatt cgaggactgg    8520
gtggcaaact acccaggagt aggggcggg tctttattg acaaccgcgt atggttccca    8580
gtttacggag ggctaaaacc caattcgccc agtgacaccg cacaagaagg gaaatatgta    8640
atatacaagc gatacaatga cacatgtcca gatgagcaag attatcagat tcaaatggct    8700
aagtcttcat ataagcctgg gcggtttgga gggaaacgcg tacagcaggc catcttatct    8760
atcaaagtgt caacatcctt gggcgaggac ccggtactga ctgtaccgcc caacacagta    8820
acactcatgg gggccgaagg cagagttctc acagtaggga catctcattt cctttatcag    8880
cgagggtcat catacttctc ccctgcccta ctatatccta tgatagtcag caacaaaaca    8940
gccactcttc atagtcctta tacattcaat gccttcactc gaccaggtag tgtcccttgc    9000
```

```
caggcttcag caagatgccc taactcatgt gttaccggag tctatactga tccatatccc   9060
ttggtcttct ataggaacca caccttgcga ggggtattcg ggacgatgct tgatgataaa   9120
caagcaagac tcaaccctgt atctgcagta tttgacagca tatcccgcag tcgcataacc   9180
cgggtgagtt caagcagcac caaggcagca tacacaacat caacatgttt taaagttgta   9240
aagaccaata aaacctattg tctcagcatt gccgaaatat ccatacccct cttcggggaa   9300
ttcagaatcg tcccttttact agttgagatt ctcaaggatg atggggttag agaagccagg   9360
tctagccggt tgagtcaact gcgagagggt tggaaagatg acattgtatc acctatcttt   9420
tgcgacgcca agaatcaaac tgaataccgg cgcgagctcg agtcctacgc tgccagttgg   9480
ccataatcag ctagtgctaa tgtgattaga ttaagtcttg tcggtagtca cttgattaag   9540
aaaaaatgtg ggtggtagcg ggatataagg caaaacaact caaggaggat agcacgggta   9600
ggacatggcg agctccggtc ccgagagggc ggagcatcag attatcctac cagagtcaca   9660
cctgtcttca ccattagtca agcacaaact actctattac tggaaattaa ctgggctacc   9720
actccctgac gagtgtgact tcgaccacct cattctcagc cgacaatgga agaaaatact   9780
tgaatcggcc tcccctgaca ctgagagaat gataaaactt ggaagggcag tgcaccagac   9840
tctcaaccac aattccaaga taaccggagt actccatccc aggtgtttag aagaattggc   9900
tagtattgag gttcctgact caaccaacaa gtttcggaag atcgagaaga aaatccaaat   9960
tcacaacaca aggtatggag aactgttcac aagactgtgc acgcatgtag agaagaaatt  10020
gttgggatca tcttggtcta ataatgtccc ccggtcagaa gagttcaaca gcatccgtac  10080
agatccggca ttctggtttc actcaaaatg gtccacaact aagtttgcat ggctccatat  10140
aaaacagatt caaaggcatc tgattgtggc agcaagaaca aggtccgcag ccaacaaatt  10200
ggtgacgctg acccataagg taggccaagt ctttgttact cctgagcttg tcattgtgac  10260
acatacagat gagaacaagt tcacgtgtct tacccaggaa cttgtgttga tgtatgcaga  10320
tatgatggag ggcagagata tggtcaacat aatatcatcc acggcggcac atctcaggag  10380
cctatcagag aaaattgatg acattctgcg gttagtagat gccctggcaa aagatctggg  10440
taatcaagtc tacgatgttg tagcactcat ggagggattt gcatacggcg ccgtccagct  10500
gcttgagccg tcaggtacat tcgcagggga tttcttcgca ttcaacctgc aggagctcaa  10560
agacactttg atcggcctcc ttcctaagga tatagcagaa tctgtgactc acgcaatagc  10620
cactgtattc tctggcttag aacaaaatca agcggctgag atgctgtgcc tgttgcgtct  10680
atggggccac ccattacttg agtcccgtat tgcggcaaaa gcagtaagga gccaaatgtg  10740
cgcaccaaaa atggtagact ttgatatgat cctccaggta ttgtctttct ttaaaggaac  10800
aatcatcaac ggatacagaa agaagaatgc aggtgtttgg ccacgtgtca agtagatac   10860
gatatacggg aaggtcattg gcagctaca cgctgattca gcggagattt cacacgatat   10920
catgttgaga gagtacaaga gtttatctgc gcttgaattc gagccatgta tagaatacga  10980
ccctatcacc aatctgagca tgtttctaaa agacaaggcg atcgcacacc cgaaagacaa  11040
ctggctcgcc gcgtttaggc gaaaccttct ctctgaggac cagaagaaac atgtaaagga  11100
ggcaacctct actaaccgtc tcttgataga gttcttagag tcaaatgatt ttgatccata  11160
taaggagatg gaatatctga cgacccttga gtacctaaga gatgacaatg tggcagtatc  11220
atactcgctc aaggagaagg aagtgaaggt taatgggcgg atttttgcta agctaacaaa  11280
gaaattaagg aactgtcaag tgatggcgga agggatctta gctgaccaga ttgcaccttt  11340
```

```
ctttcaaggg aatggggtca ttcaggatag catatcttta accaagagta tgctagcgat   11400
gagtcaattg tctttcaaca gcaataagaa acgtatcact gactgcaaag aaagagtagc   11460
ctcaaaccgc aatcacgatc aaaagagcaa gaatcgtcgg agagttgcca cttttataac   11520
gactgacctg caaaagtact gtcttaattg gagatatcag acaatcaaac tgttcgctca   11580
tgccatcaat cagctgatgg gcttacctca cttcttcgaa tggattcatc taagactaat   11640
ggatactacg atgtttgtag gagacccttt caatccccca agtgaccaa ctgactgtga    11700 tctctcaaga gtcccaaatg atgacatata tattgtcagt gctagagggg gtattgaggg   11760
attatgtcag aagctatgga caatgatctc aattgctgca atccaacttg ctgcagcaag   11820
atcacattgt cgcgtcgcct gtatggtaca gggtgacaat caagtaatag ctgtaacgag   11880
agaggtaagg tcagatgact ccccggaaat ggtgttaaca caattgcatc aagccagtga   11940
taatttcttc aaggaattga ttcatgttaa tcatttgatt ggccataatt tgaaggatcg   12000
tgaaacaatc agatcagaca cattcttcat atacagcaaa cgaatattca agatggagc    12060 aatactcagt caagtcctca aaaattcatc taaattagtg ctaatatcag gcgaccttag   12120
tgaaaacacc gtaatgtcct gtgccaacat tgcatctact atagcacggc tgtgcgagaa   12180
cgggcttcca aaggatttct gttattactt aaactacctg atgagttgcg tgcagacata   12240
ctttgattct gagttttcca tcactaacag ctcgcacccc gattctaacc agtcgtggat   12300
tgaagacatc tcttttgtgc actcatatgt cctgaccccct gcccagctag ggggactgag   12360
caacctccaa tactcaaggc tctacacgag gaacatcggt gacccgggaa ctactgcttt   12420
tgcagagatc aagcgattag aagcagtggg gttactaagt cctagtatta tgactaacat   12480
cttaactagg ccgcctggaa atggagattg ggccagtctg tgtaacgacc cttactcttt   12540
caattttgag actgtcgcga gtccaaatat tgtccttaag aaacatacac aaagagtcct   12600
atttgaaact tgttcaaatc ccttattatc tggcgtgcat acagaggata atgaggcaga   12660
agagaaggcg ttggctgaat ttttactcaa tcaagaagta attcatccac gtgtcgcaca   12720
tgctatcatg gaagcaagct ctataggtag gaggaagcag attcaagggc ttgttgacac   12780
aacaaacacc gtaatcaaga ttgcattgac taggaggcca cttggcatca agaggctgat   12840
gcggatagtt aactactcga gcatgcatgc aatgctgttt agagacgatg ttttctcatc   12900
taacaggtct aaccaccct tagtttcctc taatatgtgt tctctgacgc tagcagacta    12960
tgcacggaat agaagctggt caccattgac ggggggtaga aagatactgg gtgtatctaa   13020
tcctgatact atagaacttg tagagggtga gatccttagc gtcagcggag gatgcacaag   13080
atgtgacagc ggagatgaac aattcacttg gttccatctt ccgagcaata tagaactgac   13140
cgatgacacc agcaagaatc ctccgatgag agtgccgtac ctcgggtcaa agactcaaga   13200
gaggagggcc gcctcgcttg cgaaaatagc tcatatgtca ccacatgtga aagctgctct   13260
aagggcatca tccgtgttga tctgggctta tggagacaac gaagtaaatt ggactgctgc   13320
tcttaaaatt gcaagatctc ggtgcaatat aaactcagag tatcttcgac tattgtcccc   13380
cttacccaca gctgggaatc tccaacatag actggatgac ggcataactc agatgacatt   13440 caccccctgca tctctctaca gggtgtcacc ttatattcac atatccaatg attctcaaag   13500
gttattcacg gaagaaggag tcaaagaggg aaatgtagtt tatcagcaaa tcatgctctt   13560
gggtttatct ctaatcgaat cactcttccc gatgacgaca accaggacat acgatgagat   13620
cacattgcac ctccacagta aatttagctg ctgtatcagg gaagcaccgg ttgcagttcc   13680
tttcgagtta ctcgggatgg caccagaact aaggacagtg acctcaaata gtttatgta    13740
```

```
tgatcctagt cctgtatcgg agggtgactt tgcgagactt gacttagcta tctttaagag   13800
ttatgagctt aatctagaat catatcccac aatagagcta atgaacattc tttcaatatc   13860
cagcgggaag ttaatcggcc agtctgtggt ttcttatgat gaagatacct ccataaagaa   13920
tgacgccata atagtgtatg acaacacccg gaattggatc agcgaagctc agaattcaga   13980
tgtggtccgc ctattcgagt atgcagcact tgaagtgctt ctcgactgtt cttatcagct   14040
ctactatctg agagtaagag gcctagacaa tatcgtgttg tatatgagtg acttatataa   14100
gaatatgcca ggaattctac tttccaacat tgcagctaca atatctcatc ccatcattca   14160
ttcaagattg catgcagtag gcctggtcaa tcacgacggg tcacaccaac ttgcagacac   14220
agatttcatc gaaatgtctg caaaactatt agtctcttgc actcgacgcg tggtctcagg   14280
tttatatgca gggaataagt atgatctgct gttcccgtct gtcttagatg ataacctgag   14340
tgagaagatg cttcagctga tatctcggtt atgctgcctg tatacggtgc tctttgctac   14400
aacaagagag atcccgaaaa taagaggctt atctgcagaa gagaagtgtt cagtacttac   14460
tgagtaccta ctgtcagatg ctgtgaaacc attacttagt tctgagcaag tgagctctat   14520
catgtctcct aacatagtta cgttcccagc taatctatat tacatgtctc ggaagagcct   14580
taatttgatt agggaaagag aggacaggga cactatcttg gcattgttgt tcccccaaga   14640
gccactactt gagttcccct tagtacaaga tattggcgct cgagtgaaag atccattcac   14700
ccgacaacct gcggcgtttt tacaagaatt agatttgagc gctccagcaa ggtatgacgc   14760
atttacactt agtcaggttc attctgaaca cacatcacca aatccggagg acgactactt   14820
agtacgatac ctgttcagag aatagggac cgcgtcctcc tcttggtata aggcatctca   14880
ccttctttct gtacctgagg tcagatgtgc aaggcacggg aattccttat acttggcaga   14940
aggaagcgga gccattatga gtcttctcga actgcatgtg ccgcatgaga ctatctatta   15000
caatacgctc ttctcaaacg agatgaaccc cccacagcgg catttcggac cgaccccaac   15060
acagtttctg aattcagttg tttataggaa tctacaggcg gaggtaccat gtaaggatgg   15120
atttgtccag gagttccgtc cattatggag agagaataca gaagaaagcg atctgacctc   15180
agataaagca gtgggttaca tcacatctgc agtgccctac cggtctgtat cattgctgca   15240
ctgtgacatt gagattcctc caggatccaa tcaaagctta ctggatcaac tggctaccaa   15300
tctgtctctg attgccatgc attctgtaag ggagggcggg gtcgtgatca tcaaagtgtt   15360
gtatgcaatg ggatattact tccatctact catgaacttg ttcactccgt gttctacgaa   15420
aggatatatt ctctctaatg gctatgcatg tagaggggat atggagtgtt acctggtatt   15480
tgtcatgggc tatcgaggtg ggcctacatt tgtacatgag gtagtgagga tggcaaaaac   15540
tctagtgcag cggcacggta cacttttgtc caaatcagat gagatcacac tgactaggtt   15600
atttacctca cagcggcagc gtgtaacaga catcctatcc agtcctttac cgagactaat   15660
aaagttcttg agaaagaata tcgatactgc gctaattgaa gccggggac aacccgtccg   15720 tccattctgt gcagagagct tggtgaggac actagcggac acaactcaga tgacccagat   15780
catcgctagt cacattgaca cagtcattcg atctgtgatc tacatggagg ctgagggtga   15840
tctcgccgac acagtgttct tatttacccc ctacaatctc tctacagacg gtaaaaagag   15900
aacatcactt aaacagtgca caaggcagat cttagaggtc acaatattgg gtcttagagt   15960
tgaaaatctc aataaagtag gtgatgtagt cagtctagta cttaaaggta tgatttctct   16020
ggaggacctg atccctctaa gaacatactt gaagcgtagt acctgcccta agtatttgaa   16080
```

-continued

```
gtctgttcta ggtattacta aactcaaaga aatgtttaca gacacctctt tattatactt    16140
gactcgtgct caacaaaaat tctacatgaa aactataggc aacgcagtca agggatacta    16200
cagtaactgt gactcttaaa gataatcaca tattaatagg ctccttttct agttaactga    16260
gcccttgttg atttaatgat actatattag aaaaaagttg cactccgatc ctttaggact    16320
cgtgttcgaa ttcaaataat tgtcttagaa aaagttgcg cgtaattgtt cttgaatgta    16380
gtcctgtcat tcaccaaatc tttgtttggt cggcatggca tctccacctc ctcgcggtcc    16440
gacctgggca tccgaaggag gacgcacgtc cactcggatg gctaagggag tagcataacc    16500
ccttggggcc tctaaacggg tcttgagggg ttttttgggc gcgccgtcga ccgatgccct    16560
tgagagcctt caacccagtc agctccttcc ggtgggcgcg gggcatgact atcgtcgccg    16620
cacttatgac tgtcttcttt atcatgcaac tcgtaggaca ggtgccggca gcgctctggg    16680
tcattttcgg cgaggaccgc tttcgctgga gcgcgacgat gatcggcctg tcgcttgcgg    16740
tattcggaat cttgcacgcc ctcgctcaag ccttcgtcac tggtcccgcc accaaacgtt    16800
tcggcgagaa gcaggccatt atccgccgca tggcggccga cgcgctgggc tacgtcttgc    16860
tggcgttcgc gacgcgaggc tggatggcct tccccattat gattcttctc gcttccggcg    16920
gcatcgggat gcccgcgttg caggccatgc tgtccaggca ggtagatgac gaccatcagg    16980
gacagcttca aggatcgctc gcggctctta ccagcctaac ttcgatcact ggaccgctga    17040
tcgtcacggc gatttatgcc gcctcggcga gcacatggaa cgggttggca tggattgtag    17100
gcgccgccct ataccttgtc tgcctccccg cgttgcgtcg cggtgcatgg agccgggcca    17160
cctcgacctg aatggaagcc ggcggcacct cgctaacgga ttcaccactc caagaattgg    17220
agccaatcaa ttcttgcgga gaactgtgaa tgcgcaaacc aaccccttggc agaacatatc    17280 catcgcgtcc gccatctcca gcagccgcac gcggcgcatc tcgggcagcg ttgggtcctg    17340
gccacgggtg cgcatgatcg tgctcctgtc gttgaggacc cggctaggct ggcggggttg    17400
ccttactggt tagcagaatg aatcaccgat acgcgagcga acgtgaagcg actgctgctg    17460
caaaacgtct gcgacctgag caacaacatg aatggtcttc ggtttccgtg tttcgtaaag    17520
tctggaaacg cggaagtcag cgccctgcac cattatgttc cggatctgca tcgcaggatg    17580
ctgctggcta ccctgtggaa cacctacatc tgtattaacg aagcgctggc attgaccctg    17640
agtgattttt ctctggtccc gccgcatcca taccgccagt tgtttaccct cacaacgttc    17700
cagtaaccgg gcatgttcat catcagtaac ccgtatcgtg agcatcctct ctcgtttcat    17760
cggtatcatt acccccatga acagaaatcc cccttacacg gaggcatcag tgaccaaaca    17820
ggaaaaaacc gcccttaaca tggcccgctt tatcagaagc cagacattaa cgcttctgga    17880
gaaactcaac gagctggacg cggatgaaca ggcagacatc tgtgaatcgc ttcacgacca    17940
cgctgatgag ctttaccgca gctgcctcgc gcgtttcggt gatgacggtg aaaacctctg    18000
acacatgcag ctcccggaga cggtcacagc ttgtctgtaa gcggatgccg ggagcagaca    18060
agcccgtcag ggcgcgtcag cgggtgttgg cgggtgtcgg ggcgcagcca tgacccagtc    18120
acgtagcgat agcggagtgt atactggctt aactatgcgg catcagagca gattgtactg    18180
agagtgcacc atatgcggtg tgaaataccg cacagatgcg taaggagaaa ataccgcatc    18240
aggcgctctt ccgcttcctc gctcactgac tcgctgcgct cggtcgttcg gctgcggcga    18300
gcggtatcag ctcactcaaa ggcggtaata cggttatcca cagaatcagg ggataacgca    18360
ggaaagaaca tgtgagcaaa aggccagcaa aaggccagga accgtaaaaa ggccgcgttg    18420
ctggcgtttt tccataggct ccgcccccct gacgagcatc acaaaaatcg acgctcaagt    18480
```

```
cagaggtggc gaaacccgac aggactataa agataccagg cgtttccccc tggaagctcc  18540
ctcgtgcgct ctcctgttcc gaccctgccg cttaccggat acctgtccgc ctttctccct  18600
tcgggaagcg tggcgctttc tcatagctca cgctgtaggt atctcagttc ggtgtaggtc  18660
gttcgctcca agctgggctg tgtgcacgaa ccccccgttc agcccgaccg ctgcgcctta  18720
tccggtaact atcgtcttga gtccaacccg gtaagacacg acttatcgcc actggcagca  18780
gccactggta acaggattag cagagcgagg tatgtaggcg gtgctacaga gttcttgaag  18840
tggtggccta actacggcta cactagaagg acagtatttg gtatctgcgc tctgctgaag  18900
ccagttacct tcgaaaaag agttggtagc tcttgatccg gcaaacaaac caccgctggt  18960
agcggtggtt ttttttgtttg caagcagcag attacgcgca gaaaaaaagg atctcaagaa  19020
gatcctttga tcttttctac ggggtctgac gctcagtgga acgaaaactc acgttaaggg  19080
attttggtca tgagattatc aaaaaggatc ttcacctaga tccttttaaa ttaaaaatga  19140
agttttaaat caatctaaag tatatatgag taaacttggt ctgacagtta ccaatgctta  19200
atcagtgagg cacctatctc agcgatctgt ctatttcgtt catccatagt tgcctgactc  19260
cccgtcgtgt agataactac gatacgggag ggcttaccat ctggccccag tgctgcaatg  19320
ataccgcgag acccacgctc accggctcca gatttatcag caataaacca gccagccgga  19380
agggccgagc gcagaagtgg tcctgcaact ttatccgcct ccatccagtc tattaattgt  19440
tgccgggaag ctagagtaag tagttcgcca gttaatagtt tgcgcaacgt tgttgccatt  19500
gctgcaggca tcgtggtgtc acgctcgtcg tttggtatgg cttcattcag ctccggttcc  19560
caacgatcaa ggcgagttac atgatccccc atgttgtgca aaaaagcggt tagctccttc  19620
ggtcctccga tcgttgtcag aagtaagttg gccgcagtgt tatcactcat ggttatggca  19680
gcactgcata attctcttac tgtcatgcca tccgtaagat gcttttctgt gactggtgag  19740
tactcaacca agtcattctg agaatagtgt atgcggcgac cgagttgctc ttgcccggcg  19800
tcaacacggg ataataccgc gccacatagc agaactttaa aagtgctcat cattggaaaa  19860
cgttcttcgg ggcgaaaact ctcaaggatc ttaccgctgt tgagatccag ttcgatgtaa  19920
cccactcgtg cacccaactg atcttcagca tcttttactt tcaccagcgt ttctgggtga  19980
gcaaaaacag gaaggcaaaa tgccgcaaaa aagggaataa gggcgacacg gaaatgttga  20040
atactcatac tcttcctttt tcaatattat tgaagcattt atcagggtta ttgtctcatg  20100
agcggataca tatttgaatg tatttagaaa aataaacaaa tagggggttcc gcgcacattt  20160
ccccgaaaag tgccacctga cgtctaagaa accattatta tcatgacatt aacctataaa  20220
aataggcgta tcacgaggcc ctttcgtctt caagaattct aatacgactc actatagg    20278
```

<210> SEQ ID NO 3  
<211> LENGTH: 197  
<212> TYPE: PRT  
<213> ORGANISM: Artificial Sequence  
<220> FEATURE:  
<223> OTHER INFORMATION: RBD protein

<400> SEQUENCE: 3

```
Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45
```

```
Cys Tyr Gly Val Ser Pro Thr Lys Leu Asn Asp Leu Cys Phe Thr Asn
 50                  55                  60

Val Tyr Ala Asp Ser Phe Val Ile Arg Gly Asp Glu Val Arg Gln Ile
 65                  70                  75                  80

Ala Pro Gly Gln Thr Gly Lys Ile Ala Asp Tyr Asn Tyr Lys Leu Pro
                 85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Leu Ser Phe Glu Leu Leu His Ala Pro Ala
            180                 185                 190

Thr Val Cys Gly Pro
        195

<210> SEQ ID NO 4
<211> LENGTH: 117
<212> TYPE: PRT
<213> ORGANISM: Artificial Sequence
<220> FEATURE:
<223> OTHER INFORMATION: F2 subunit

<400> SEQUENCE: 4

Met Gly Ser Arg Ser Ser Thr Arg Ile Pro Val Pro Leu Met Leu Thr
  1               5                  10                  15

Val Arg Val Met Leu Ala Leu Ser Cys Val Cys Pro Thr Ser Ala Leu
                 20                  25                  30

Asp Gly Arg Pro Leu Ala Ala Gly Ile Val Val Thr Gly Asp Lys
             35                  40                  45

-continued

```
                20                  25                  30
```

<210> SEQ ID NO 6
<211> LENGTH: 15
<212> TYPE: PRT
<213> ORGANISM: Artificial Sequence
<220> FEATURE:
<223> OTHER INFORMATION: fusion peptide

<400> SEQUENCE: 6

```
Ile Gly Ala Ile Ile Gly Gly Val Ala Leu Gly Val Ala Thr Ala
1               5                   10                  15
```

<210> SEQ ID NO 7
<211> LENGTH: 55
<212> TYPE: PRT
<213> ORGANISM: Artificial Sequence
<220> FEATURE:
<223> OTHER INFORMATION: transmembrane domain

<400> SEQUENCE: 7

```
Ser Ala Leu Ile Thr Tyr Ile Val Leu Thr Val Ile Ser Leu Val Cys
1               5                   10                  15

Gly Ile Leu Ser Leu Val Leu Ala Cys Tyr Leu Met Tyr Lys Gln Lys
            20                  25                  30

Ala Gln Gln Lys Thr Leu Leu Trp Leu Gly Asn Asn Thr Leu Asp Gln
        35                  40                  45

Met Arg Ala Thr Thr Lys Met
    50                  55
```

<210> SEQ ID NO 8
<211> LENGTH: 2
<212> TYPE: PRT
<213> ORGANISM: Artificial Sequence
<220> FEATURE:
<223> OTHER INFORMATION: kozak sequence

<400> SEQUENCE: 8

```
Ala Thr
1
```

<210> SEQ ID NO 9
<211> LENGTH: 30
<212> TYPE: DNA
<213> ORGANISM: Artificial Sequence
<220> FEATURE:
<223> OTHER INFORMATION: L2 forward primer

<400> SEQUENCE: 9
acgcgtggtc tcaggtttat atgcagggaa                                    30

<210> SEQ ID NO 10
<211> LENGTH: 31
<212> TYPE: DNA
<213> ORGANISM: Artificial Sequence
<220> FEATURE:
<223> OTHER INFORMATION: L2 reverse primer

<400> SEQUENCE: 10
ttaattaaac caaacaaaga tttggtgaat g                                  31

<210> SEQ ID NO 11
<211> LENGTH: 30
<212> TYPE: DNA
<213> ORGANISM: Artificial Sequence

```
<220> FEATURE:
<223> OTHER INFORMATION: L1 forward primer

<400> SEQUENCE: 11
actagttgag attctcaagg atgatggggt                              30

<210> SEQ ID NO 12
<211> LENGTH: 30
<212> TYPE: DNA
<213> ORGANISM: Artificial Sequence
<220> FEATURE:
<223> OTHER INFORMATION: L1 reverse primer

<400> SEQUENCE: 12
acgcgtcgag tgcaagagac taatagtttt                              30

<210> SEQ ID NO 13
<211> LENGTH: 29
<212> TYPE: DNA
<213> ORGANISM: Artificial Sequence
<220> FEATURE:
<223> OTHER INFORMATION: F-HN forward primer

<400> SEQUENCE: 13
ggcgccatta tcggtggtgt agctctcgg                               29

<210> SEQ ID NO 14
<211> LENGTH: 30
<212> TYPE: DNA
<213> ORGANISM: Artificial Sequence
<220> FEATURE:
<223> OTHER INFORMATION: F-HN reverse primer

<400> SEQUENCE: 14
actagtaaag ggacgattct gaattccccg                              30

<210> SEQ ID NO 15
<211> LENGTH: 30
<212> TYPE: DNA
<213> ORGANISM: Artificial Sequence
<220> FEATURE:
<223> OTHER INFORMATION: P-M-F forward primer

<400> SEQUENCE: 15
ccgcggaaac agccaagaga gaccgcagaa                              30

<210> SEQ ID NO 16
<211> LENGTH: 33
<212> TYPE: DNA
<213> ORGANISM: Artificial Sequence
<220> FEATURE:
<223> OTHER INFORMATION: P-M-F reverse primer

<400> SEQUENCE: 16
ggcgccaacc gggatccaga atcttctacc cgt                          33

<210> SEQ ID NO 17
<211> LENGTH: 30
<212> TYPE: DNA
<213> ORGANISM: Artificial Sequence
<220> FEATURE:
<223> OTHER INFORMATION: NP-P forward primer

<400> SEQUENCE: 17
gtttaaacac caaacagaga atccgtaagg                              30
```

<210> SEQ ID NO 18
<211> LENGTH: 30
<212> TYPE: DNA
<213> ORGANISM: Artificial Sequence
<220> FEATURE:
<223> OTHER INFORMATION: NP-P reverse primer

<400> SEQUENCE: 18
ccgcggcttt gttgactccc ctgttgttga                                    30

<210> SEQ ID NO 19
<211> LENGTH: 20
<212> TYPE: DNA
<213> ORGANISM: Artificial Sequence
<220> FEATURE:
<223> OTHER INFORMATION: pBR322-NP forward primer

<400> SEQUENCE: 19
ttctcgcttc cggcggcatc                                               20

<210> SEQ ID NO 20
<211> LENGTH: 47
<212> TYPE: DNA
<213> ORGANISM: Artificial Sequence
<220> FEATURE:
<223> OTHER INFORMATION: pBR322-NP reverse primer

<400> SEQUENCE: 20
ccgcttctac ccgtattttt tctaagcaga ggaattggga tgacctc                 47

<210> SEQ ID NO 21
<211> LENGTH: 48
<212> TYPE: DNA
<213> ORGANISM: Artificial Sequence
<220> FEATURE:
<223> OTHER INFORMATION: P-M forward primer

<400> SEQUENCE: 21
tacgggtaga agcggccgcg gccggcccca caccccaccc ctcaatcc               48

<210> SEQ ID NO 22
<211> LENGTH: 23
<212> TYPE: DNA
<213> ORGANISM: Artificial Sequence
<220> FEATURE:
<223> OTHER INFORMATION: P-M reverse primer

<400> SEQUENCE: 22
ccgggatcca gaatcttcta ccc                                           23

<210> SEQ ID NO 23
<211> LENGTH: 21
<212> TYPE: DNA
<213> ORGANISM: Artificial Sequence
<220> FEATURE:
<223> OTHER INFORMATION: F-HN forward primer

<400> SEQUENCE: 23
gattctggat cccggttggc g                                             21

<210> SEQ ID NO 24
<211> LENGTH: 21
<212> TYPE: DNA
<213> ORGANISM: Artificial Sequence
<220> FEATURE:
<223> OTHER INFORMATION: F-HN reverse primer

<400> SEQUENCE: 24
ccgccatcac ttgacagttc c                                    21

<210> SEQ ID NO 25
<211> LENGTH: 20
<212> TYPE: DNA
<213> ORGANISM: Artificial Sequence
<220> FEATURE:
<223> OTHER INFORMATION: L forward primer

<400> SEQUENCE: 25
gtcaagtgat ggcggaaggg                                      20

<210> SEQ ID NO 26
<211> LENGTH: 20
<212> TYPE: DNA
<213> ORGANISM: Artificial Sequence
<220> FEATURE:
<223> OTHER INFORMATION: L reverse primer

<400> SEQUENCE: 26
cgccggaagc gagaagaatc                                      20

<210> SEQ ID NO 27
<211> LENGTH: 23
<212> TYPE: DNA
<213> ORGANISM: Artificial Sequence
<220> FEATURE:
<223> OTHER INFORMATION: NDV check forward primer

<400> SEQUENCE: 27
ccacaattcc aagataaccg gag                                  23

<210> SEQ ID NO 28
<211> LENGTH: 23
<212> TYPE: DNA
<213> ORGANISM: Artificial Sequence
<220> FEATURE:
<223> OTHER INFORMATION: NDV check reverse primer

<400> SEQUENCE: 28
gctgccacaa tcagatgcct ttg                                  23

<210> SEQ ID NO 29
<211> LENGTH: 21
<212> TYPE: DNA
<213> ORGANISM: Artificial Sequence
<220> FEATURE:
<223> OTHER INFORMATION: RBD check forward primer

<400> SEQUENCE: 29
gtcagacaaa tcgctccagg g                                    21

<210> SEQ ID NO 30
<211> LENGTH: 21
<212> TYPE: DNA
<213> ORGANISM: Artificial Sequence
<220> FEATURE:
<223> OTHER INFORMATION: RBD check reverse primer

<400> SEQUENCE: 30
aggtccacaa acagttgctg g                                    21

<210> SEQ ID NO 31

```
<211> LENGTH: 25
<212> TYPE: DNA
<213> ORGANISM: Artificial Sequence
<220> FEATURE:
<223> OTHER INFORMATION: Vaccinia virus check forward primer

<400> SEQUENCE: 31
atgacgatga aaatgatggt acata                                                25

<210> SEQ ID NO 32
<211> LENGTH: 25
<212> TYPE: DNA
<213> ORGANISM: Artificial Sequence
<220> FEATURE:
<223> OTHER INFORMATION: Vaccinia virus check reverse primer

<400> SEQUENCE: 32
ctccaatact actgtagttg taagg                                                25
```